United States Patent
Berryman et al.

(10) Patent No.: US 9,408,684 B2
(45) Date of Patent: Aug. 9, 2016

(54) SYSTEMS AND METHODS FOR INCONTINENCE CONTROL

(71) Applicant: SOFT HEALTH TECHNOLOGIES LLC, Aliso Viejo, CA (US)

(72) Inventors: Thomas J. Berryman, Laguna Beach, CA (US); John M. Taylor, Trabuco Canyon, CA (US)

(73) Assignee: SOFT HEALTH TECHNOLOGIES, LLC, Irvine, CA (US)

( * ) Notice: Subject to any disclaimer, the term of this patent is extended or adjusted under 35 U.S.C. 154(b) by 0 days.

(21) Appl. No.: 14/870,104

(22) Filed: Sep. 30, 2015

(65) Prior Publication Data

US 2016/0095684 A1 Apr. 7, 2016

Related U.S. Application Data

(60) Provisional application No. 62/059,833, filed on Oct. 3, 2014.

(51) Int. Cl.
*A61F 2/00* (2006.01)
*A61F 13/472* (2006.01)
*A61L 15/18* (2006.01)
(Continued)

(52) U.S. Cl.
CPC ......... *A61F 2/0009* (2013.01); *A61F 13/00063* (2013.01); *A61F 13/47209* (2013.01); *A61F 13/47227* (2013.01); *A61L 15/18* (2013.01); *A61L 15/28* (2013.01); *A61L 15/58* (2013.01); *A61F 2013/15121* (2013.01); *A61F 2210/00* (2013.01); *A61F 2230/0063* (2013.01);

(Continued)

(58) Field of Classification Search
CPC ....... A61F 2/0004; A61F 2/0009; A61F 5/44; A61F 5/48; A61F 13/15
USPC ........ 600/29–32; 128/DIG. 25; 604/358, 359, 604/385.01, 385.17
See application file for complete search history.

(56) References Cited

U.S. PATENT DOCUMENTS

| 4,593,053 A | 6/1986 | Jevne et al. |
| 5,074,855 A | 12/1991 | Rosenbluth et al. |

(Continued)

FOREIGN PATENT DOCUMENTS

| JP | 2005-065750 A | 3/2005 |
| JP | 2005-160845 A | 6/2005 |

OTHER PUBLICATIONS

Brubaker, L., Harris, T., Gleason, D., Newman, D., North, B., Miniguard Investigation Group, "The External Urethral Barrier for Stress Incontinence: A Multicenter Trial of Safety and Efficacy", Obstetrics & Gynecology, Jun. 1999, pp. 932-937, vol. 93, No. 6, Elsevier, New York, USA.

(Continued)

*Primary Examiner* — John Lacyk
(74) *Attorney, Agent, or Firm* — Blair Walker IP Services, LLC

(57) ABSTRACT

A system for managing female incontinence includes a body of biocompatible material configured to fit between the labia minora and the vestibule floor, the body having a surface configured to occlude the urethral meatus, an adhesive carried on at least a first portion of the surface and configured to provide a sealing engagement between the body and the urethral meatus, and a substance carried by at least one of the body and the adhesive and configured for controlling the odor of the general vaginal-urethral area of a female.

30 Claims, 10 Drawing Sheets

(51) Int. Cl.
*A61L 15/28* (2006.01)
*A61L 15/58* (2006.01)
*A61F 13/00* (2006.01)
*A61F 13/15* (2006.01)

(52) U.S. Cl.
CPC .................. *A61F2250/0078* (2013.01); *A61F 2310/00389* (2013.01)

(56) References Cited

U.S. PATENT DOCUMENTS

| | | | |
|---|---|---|---|
| 5,171,302 | A | 12/1992 | Buell |
| 5,197,959 | A | 3/1993 | Buell |
| 5,270,358 | A | 12/1993 | Asmus |
| 5,336,208 | A | 8/1994 | Rosenbluth et al. |
| 5,508,317 | A | 4/1996 | Müller |
| 5,769,091 | A * | 6/1998 | Simon .................. A61F 2/0009 128/885 |
| 5,885,265 | A | 3/1999 | Osborn, III et al. |
| 5,927,282 | A | 7/1999 | Lenker et al. |
| 6,131,575 | A | 10/2000 | Lenker et al. |
| 6,355,022 | B1 * | 3/2002 | Osborn, III ....... A61F 13/47209 604/330 |
| 6,432,096 | B1 | 8/2002 | McFall et al. |
| 6,461,340 | B1 | 10/2002 | Lenker et al. |
| 6,613,955 | B1 | 9/2003 | Lindsay et al. |
| 6,800,225 | B1 | 10/2004 | Hagmann et al. |
| 8,163,206 | B2 | 4/2012 | Chang et al. |
| 2001/0021833 | A1 | 9/2001 | Schmidt et al. |
| 2001/0026810 | A1 | 10/2001 | McGhee et al. |
| 2003/0100877 | A1 * | 5/2003 | Erdman ............ A61F 13/15577 604/385.23 |
| 2003/0191442 | A1 | 10/2003 | Bewick-Sonntag et al. |
| 2004/0266302 | A1 | 12/2004 | DiSalvo et al. |
| 2009/0182296 | A1 | 7/2009 | Dennis et al. |
| 2009/0221980 | A1 * | 9/2009 | Mosbacher ............ A61F 13/42 604/385.01 |
| 2010/0198177 | A1 | 8/2010 | Yahiaoui et al. |
| 2011/0008277 | A1 | 1/2011 | Bruggeman et al. |
| 2011/0086077 | A1 | 4/2011 | McCrea et al. |
| 2012/0026458 | A1 | 2/2012 | Qiu et al. |
| 2014/0350348 | A1 | 11/2014 | Tee et al. |
| 2015/0094393 | A1 | 4/2015 | Holland et al. |

OTHER PUBLICATIONS

Toumanides, S., Sideris, E., Agricola, T., Moulopoulos, S., "Transcatheter Patch Occlusion of the Left Atrial Appendage Using Surgical Adhesives in High-Risk Patients with Atrial Fibrillation", Journal of the American College of Cardiology, Nov. 15, 2011, pp. 2236-2240, vol. 58, No. 21, Elsevier, New York, USA.
Weeks, A., Morrison, D., Alauzun, J., Brook, M., Jones, L., Sheardown, H., "Photocrosslinkable hyaluronic acid as an internal wetting agent in model conventional and silicone hydrogel contact lenses", Journal of Biomedical Materials Research A, Aug. 2012, pp. 1972-1982, vol. 100A, No. 8, John Wiley & Sons, Hoboken, USA.
"The world's smallest humidity and temperature sensor", Sensirion, downloaded from the internet Aug. 27, 2014, www.sensirion.com/en/kunden-newsletter-artikel/sensirion-sensor-news-november-2012/the-worlds-smallest-humidity-and-temperature-sensor.
PCT International Search Report and Written Opinion for PCT/US2015/053367, Applicant: Soft Health Technologies, LLC, Forms PCT/ISA/220, 210, and 237 dated Feb. 4, 2016 (14 pages).
JP 2005-065750A, Shinohara et al., published Mar. 7, 2005. English translation of paragraphs [0004], [0049], [0055], [0132], [0133], [0134], [0141], [0146], [0147], [0148], [0149], [0150], [0151], [0153], [0156], [0157], [0180], [0188], [0189], [0202], [0203], [0227], [0228], [0229], [0230], [0231], [0232].

* cited by examiner

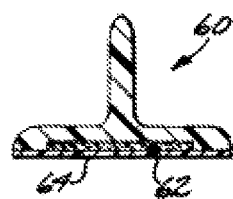
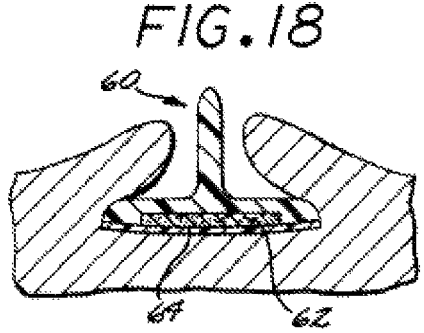
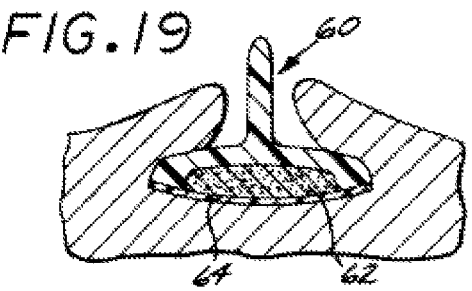
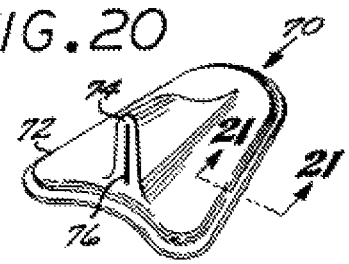
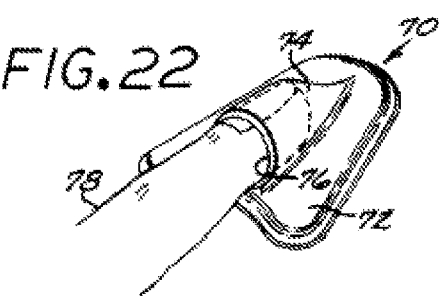
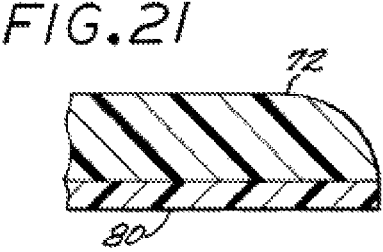
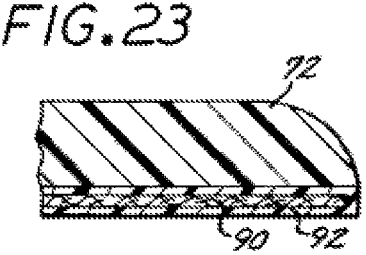
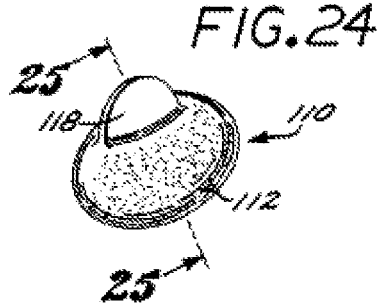
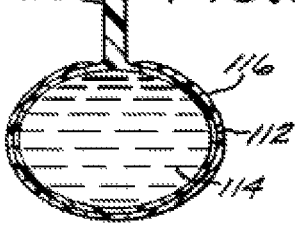

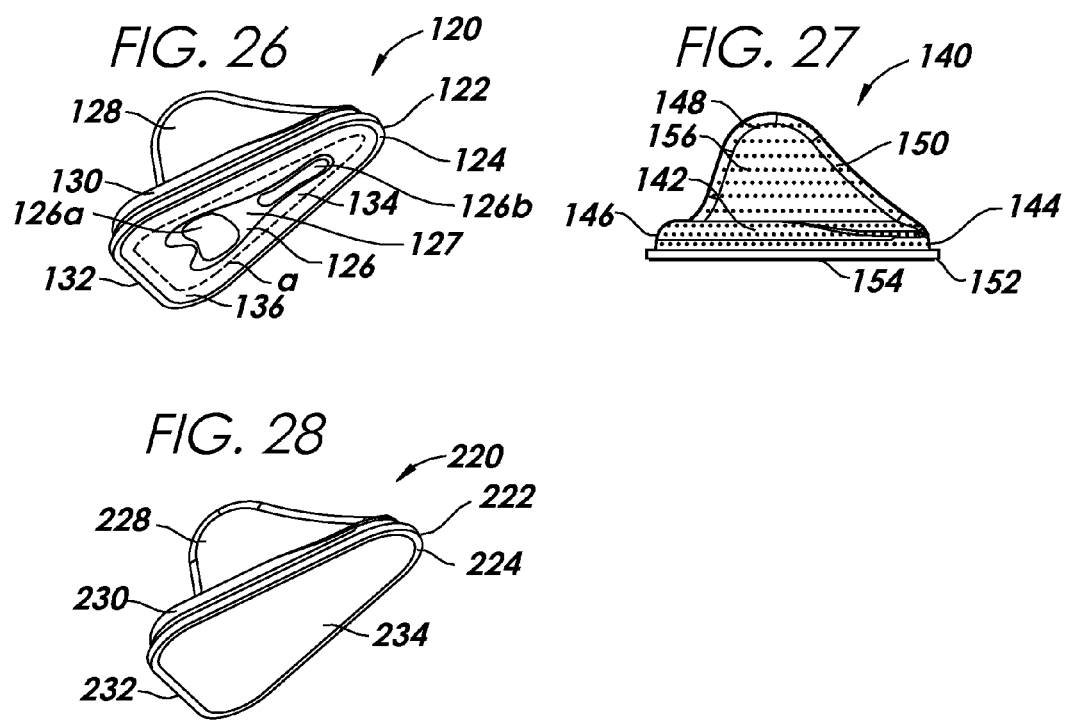

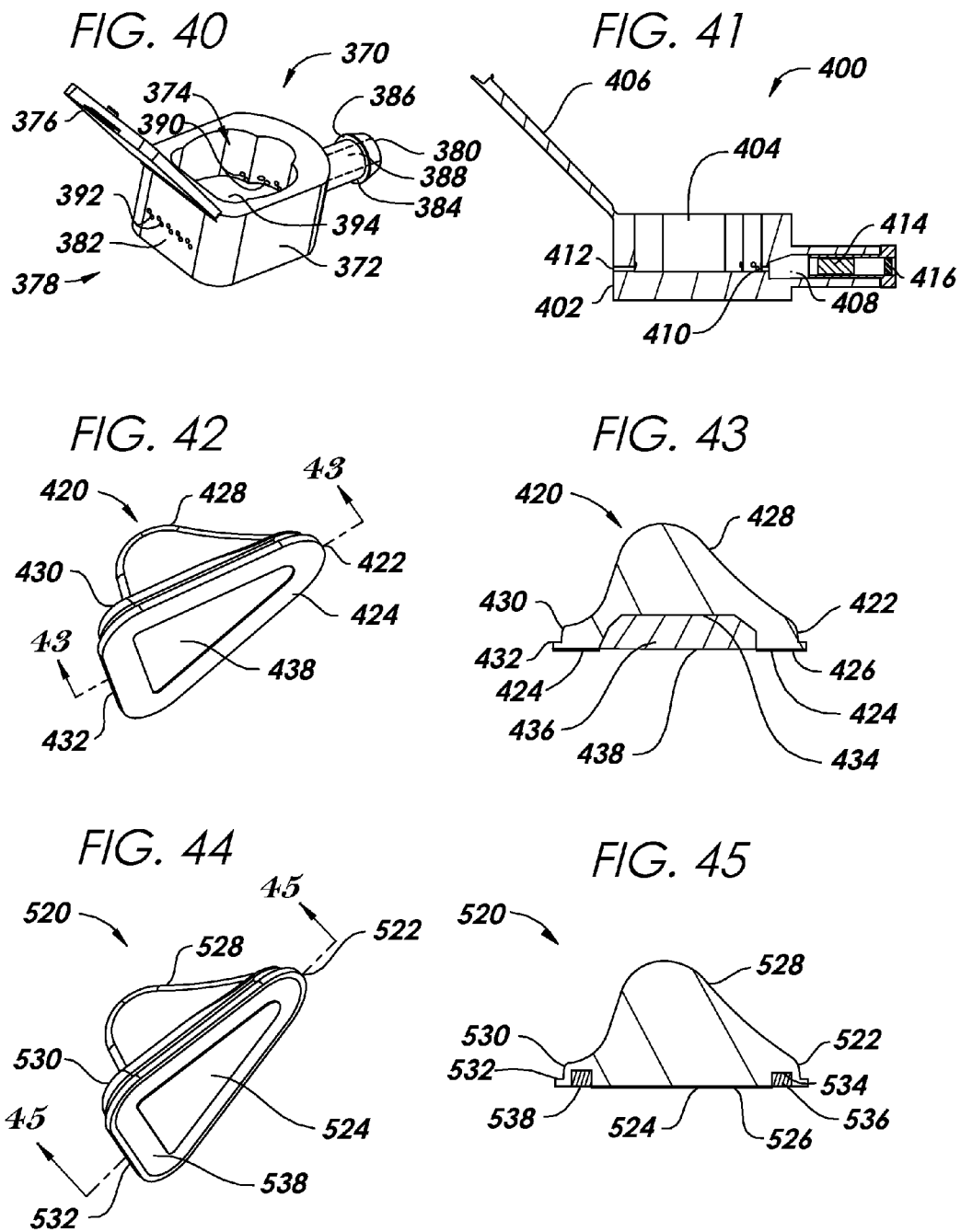

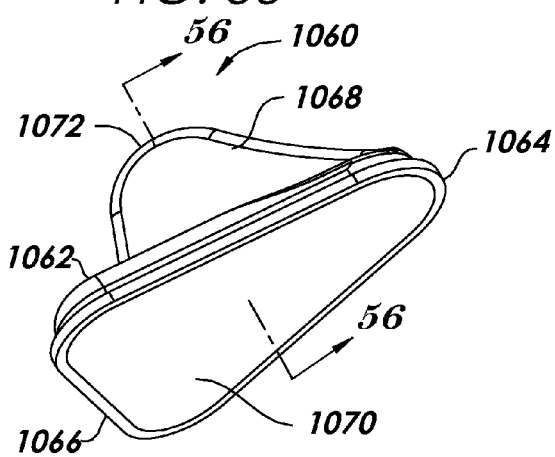
FIG. 55
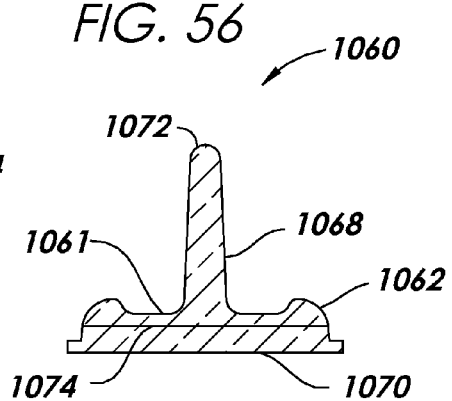
FIG. 56
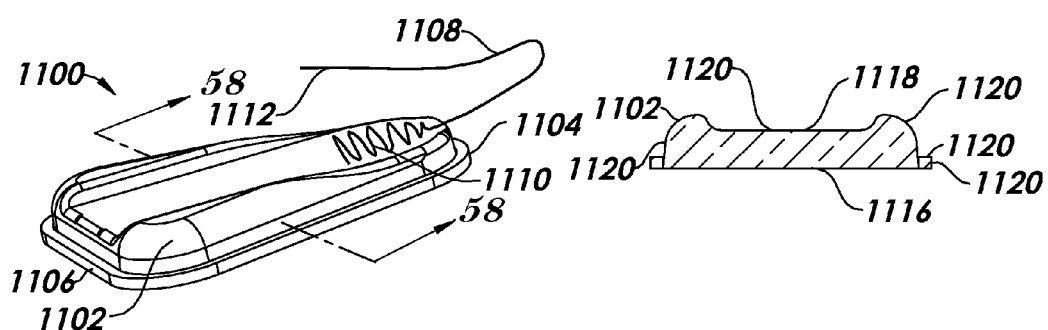
FIG. 57
FIG. 58
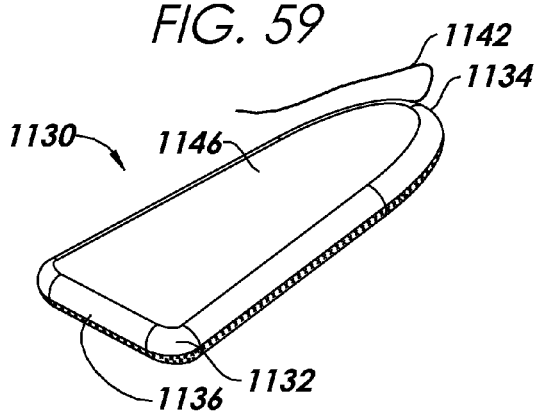
FIG. 59
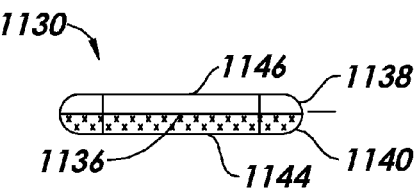
FIG. 60

27
SYSTEMS AND METHODS FOR INCONTINENCE CONTROL

INCORPORATION BY REFERENCE TO ANY PRIORITY APPLICATIONS

This application claims the benefit of priority to U.S. Provisional Application No. 62/059,833, filed on Oct. 3, 2014, which is incorporated in its entirety by reference herein for all purposes. Priority is claimed pursuant to 35 U.S.C. §119.

FIELD OF THE INVENTION

The field of the invention generally relates to devices for treating urinary incontinence.

BACKGROUND

Urinary incontinence is a troublesome problem for many individuals. Urinary stress incontinence is a particular form of urinary incontinence wherein a physical occurrence may cause unwanted leakage of urine. For example, a sudden spike in abdominal pressure from sneezing, coughing or exercise may exceed the resistive pressure of the urethra for a brief moment, causing an involuntary leakage of urine. Stress urinary incontinence occurs predominantly in adult women, but may also occur in certain male or in younger females.

Absorbent pads are available which absorb urine after it has leaked and contain it within the wearer's undergarments. Adult diapers or absorbent panties or underwear may also be used to absorb the urine. Plastic pants designed to fit over undergarments are another means of protecting outer clothing for urine which has leaked. All of these products have the disadvantage of being forced to contain the wetness and odor of leaked urine.

More recently, urinary incontinence pads which are adhesively applied directly over the urethral meatus have been used in women with the intent of more completely sealing the urethra, and preventing the involuntary leakage of urine.

SUMMARY OF THE INVENTION

In a first embodiment of the invention, a system managing female incontinence includes a body of biocompatible material configured to fit between the labia minora and the vestibule floor, the body having a surface configured to occlude the urethral meatus, an adhesive carried on at least a first portion of the surface and configured to provide a sealing engagement between the body and the urethral meatus, and a substance carried by at least one of the body and the adhesive and configured for controlling the odor of the general vaginal-urethral area of a female.

BRIEF DESCRIPTION OF THE DRAWINGS

FIG. 17 is a cross-sectional view of a fourth modification of the first embodiment, wherein the female urinary incontinence device includes a layer of super-absorbent material.
FIG. 18 is a cross-sectional view, similar to that of FIG. 17, showing the female urinary incontinence device as installed in the external genitalia of a human female.
FIG. 19 is a cross-sectional view, similar to that of FIG. 18, showing the super-absorbent material after it has absorbed moisture.
FIG. 20 is a perspective view of a fifth modified form of the first embodiment, which includes a finger hole.
FIG. 21 is a cross-sectional view, taken along Line 21-21 of FIG. 20.
FIG. 22 is a perspective view, similar to that of FIG. 20, showing the female urinary incontinence device with a human finger inserted into the finger hole.
FIG. 23 is a cross-sectional view, similar to that of FIG. 21, showing a sixth modification of the first embodiment.
FIG. 24 is a perspective view of a third embodiment.
FIG. 25 is a cross-sectional view taken along Line 25-25 of FIG. 24.
FIG. 26 is a perspective view of an embodiment of a female urinary incontinence device having variable characteristics.
FIG. 27 is a side elevational view of an embodiment of a biodegradable female urinary incontinence device.
FIG. 28 is a perspective view of an embodiment of a female urinary incontinence device having variable characteristics.

FIG. 40 is a perspective view of an embodiment of a container for a urinary incontinence device.

FIG. 41 is a cross-sectional view of an embodiment of a container for a urinary incontinence device.

FIG. 42 is a perspective view of an embodiment of a female urinary incontinence device.

FIG. 43 is a cross-sectional view of the female urinary incontinence device of FIG. 42 taken along line 43-43 of FIG. 42.

FIG. 44 is a perspective view of an embodiment of a female urinary incontinence device.

FIG. 45 is a cross-sectional view of the female urinary incontinence device of FIG. 44 taken along line 45-45 of FIG. 44.

FIG. 55 is a perspective view of an embodiment of a female urinary incontinence device.

FIG. 56 is a cross-sectional view of the female urinary incontinence device of FIG. 55 taken along line 56-56 of FIG. 55.

FIG. 57 is a perspective view of an embodiment of a female urinary incontinence device.

FIG. 58 is a cross-sectional view of the female urinary incontinence device of FIG. 57 taken along line 58-58 of FIG. 57.

FIG. 59 is a perspective view of an embodiment of a female urinary incontinence device.

FIG. 60 is a posterior elevation view of the female urinary incontinence device of FIG. 59.

DETAILED DESCRIPTION

Referring first to FIGS. 1 through 4 of the drawings, a female urinary incontinence device 10, in accordance with a first embodiment, is shown. The device comprises a body 12, formed of a resilient foam material that is biocompatible. One suitable class of materials is that of foams formed from the water actuation of prepolymers based on either toluene diisocyanate (TDI) or methylene diphenyl diisocyanate (MDI). Such prepolymers are marketed by the Dow Chemical Company, Midland, Mich., under the trademarks "HYPOL" (TDI), "HYPOL PLUS" (MDI) and "HYPOL 2002" (TDI and MDI).

Alternatively, the body 12 can be made of a biodegradable material, such as a cellulose or cotton fiber. A polyurethane foam can also be used, being rendered biodegradable by hydrolysis of a weak backbone link, such as an amine group. Other foam materials, such as polyolefins, can be used and made hydrolytically biodegradable by using weak links such as starches in the polymer backbones.

Figure 2:
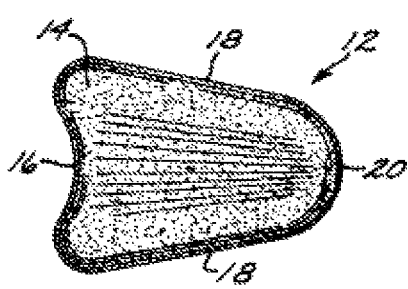
FIG. 2 is a bottom plan view of the device of FIG. 1.
Figure 4:
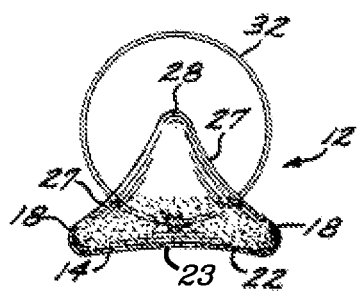
FIG. 4 is an anterior elevational view of the device of FIG. 1.
Figure 7:
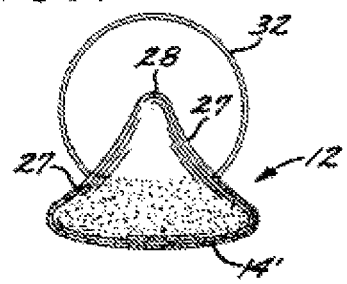
FIG. 7 is an anterior elevational view of a first modified form of the first embodiment.

The body 12 includes a base 14 that has the general outline of a blunt arrowhead, as shown in FIG. 2. In the first embodiment, the base 14 may be slightly concave, as shown in FIG. 4. Alternatively, the base 14 can be made slightly convex, as shown in FIG. 7, for those users who might find such a configuration more comfortable to wear. The base 14 may have a concave posterior end 16, as shown in FIG. 2, with lateral edges 18 that taper slightly toward each other as they extend toward a rounded anterior end 20. The anterior end 20 is thus somewhat narrower than the posterior end 16.

Figure 5:
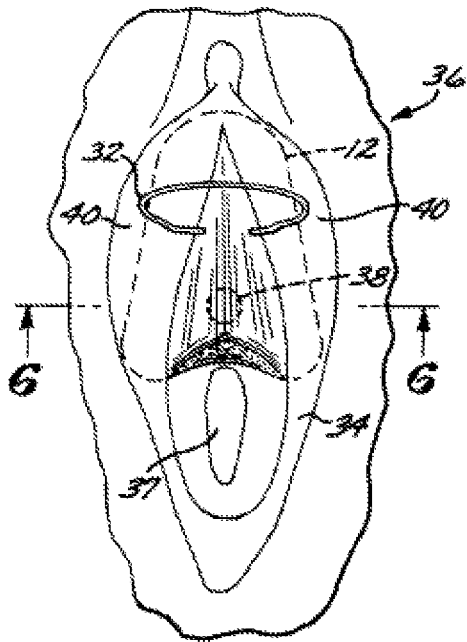
FIG. 5 is plan view of the device of FIG. 1, showing the device installed in the external genitalia of a human female.
Figure 6:
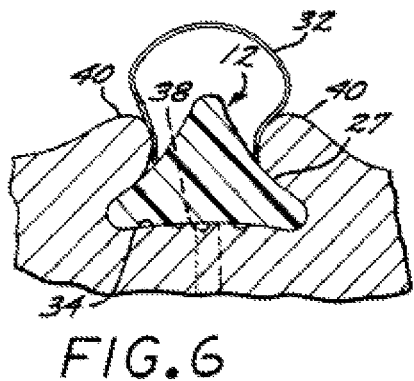
FIG. 6 is a cross-sectional view taken along line 6-6 of FIG. 5.

The body 12 is provided with an adhesive surface 23 for retention against the floor of the vestibule 34 of the vulva 36 as described in relation with FIGS. 5 and 6. In this embodiment, the base 14 is coated with an adhesive layer 22, comprising a pressure-sensitive, hydrophilic hydrogel adhesive material. Such hydrogel adhesives are marketed by R & D Medical Products, Lake Forest, Calif., under the trademark "PROMEON". The hydrogel composition may include from about 25 to about 50 weight percent polyvinyl pyrrolidone (PVP) or about 30 to about 40 weight percent. The polyvinyl pyrrolidone may have a weight average molecular weight in the range of about 100,000 to 600,000, or in the range of about 300,000 to 400,000. A suitable polyvinyl pyrrolidone is type NP-K90 commercially available from Irvine Scientific, Santa Ana, Calif.

The composition may also include polyvinyl alcohol in a weight percentage of about 2 to about 5 or about 3 to about 4 weight percent. A particular polyvinyl alcohol is sold by the E. I. DuPont de Nemours & Co. under the trade designation "Elvanol HV". Generally speaking, polyvinyl alcohol suitably may have a weight average molecular weight in the range of about 150,000 to about 300,000, or about 170,000 to about 220,000. A particular PVA is the material available from E. I. du Pont de Nemours & Co. having a stated molecular weight of about 185,000.

The polyvinyl alcohols may be generally at least about 75% hydrolyzed. PVA may be about 100% hydrolyzed.

The composition may also include about 5 to about 40 weight percent, or about 15 to about 25 weight percent polar plasticizer or humectant e.g., glycerol. Other useful polar plasticizers include propylene glycol, sorbitol, poly(ethylene)glycol, for example having a molecular weight in the range of about 200 to about 20,000, or polypropylene glycol, for example having a molecular weight in the range of about 500 to about 5,000. Other polar plasticizers or humectants will be well-known to one skilled in the hydrogel art.

The composition may also include the presence of about 3 to about 50 weight percent water in the resulting matrix. Deionized water is may be used. This percentage of water may provide suitable adhesiveness, tack, cohesive strength, and skin-compatibility.

One skilled in the art will recognize that it is possible to add small amounts of other materials to adjust the properties of the present composition for a particular end use. For example, if it is chosen to increase the tackiness of the gel, poly-2-acrylamido 2-methyl propane sulfonic acid poly (AMPS) (or its salts) may be employed. Other material which can be employed to increase tackiness include polyacrylic acid, polystyrene sulfonic acid or salts thereof, karaya, xanthan, guar or locust bean gums. Tackifiers above described may generally be present in the range of about 2 to about 20 weight percent.

For some applications, it may be chosen to increase the internal coherence, cohesiveness or strength of the present biomedical composition. In such instances, materials such as hydroxy propyl methyl cellulose, carboxy methyl cellulose, hydroxy propyl guar, dextran or silica may be added. One skilled in the art will recognize other materials which could be added to the composition described herein to adjust various desired properties. Generally speaking, such additives may be present in the range of about 0 to about 10 weight percent.

For preparation of the materials, generally speaking, a temperature-controlled, stirrable reactor may be employed. The a reactor may be preheated to about 90° C., set to mix at approximately 100 revolutions per minute, and the following materials (in representative quantities):
1. deionized $H_2O$—39 weight percent
2. glycerol polar plactizers (Mallinckrodt, Inc.)—22 weight percent
3. polyvinyl alcohol (duPont Elvanol HV)—4 weight percent
4. polyvinyl pyrrolidone (R & D Medical Products)—35 weight percent
would be mixed, for example in the order indicated. The temperature of the closed mixer then would be increased to approximately 130° C. while maintaining stirring. After a temperature of approximately 130° C. is obtained, the temperature of the mixture would be decreased to approximately 95° C., the mixer subsequently turned off and the material poured onto a release paper (e.g., "Polyslick"), the gel thereby being cooled to a solid, non-liquid state.

Another type of adhesive that has shown good results is a mixture of poly 2-hydroxyethyl methacrylate (PHEMA) and polyethylene glycol (PEG) as a plasticizer. The percentage of PHEMA may range from about 45% to about 75%, with a corresponding range of PEG of about 55% to about 25%. A particular composition is about 53% to about 54% PHEMA and about 47% to about 46% PEG. Lower percentages of PHEMA yield greater adhesiveness, while higher percentages of PHEMA yield greater durability. The PEG may have a molecular weight between about 400 and about 1000. The PHEMA may be a mixture of low molecular weight PHEMA (molecular weight between about 10,000 and about 100,000) and high molecular weight PHEMA (molecular weight greater than about 100,000). The low molecular weight PHEMA provides adhesive properties, while the high molecular weight PHEMA improves adhesive structural integrity. The PHEMA mixture may be between about 10% to about 50% low molecular weight PHEMA and between about 90% and about 50% high molecular weight PHEMA, with the precise mixture being determined by the particular adhesive properties desired.

While a possible plasticizer is PEG, as described above, other plasticizers can be used, such as propylene glycol, polypropylene glycol (PPG), or glycerin.

If the body 12 is made of TDI or MDI, the material of the body 12 itself can be rendered adhesive by combining the TDI or MDI one-to-one by weight with about 0.25 to about 0.50 molar ammonium hydroxide during the water actuation of the foam. The resulting material has a surface that is positively charged, so that it will adhere to a negatively-charged mucoid surface (such as the surface of the vestibule 34 and the inner portions of the labia minora).

Alternatively, the entire body 12 can be formed of an adhesive, such as the PHEMA/PEG mixture described above. In many medical or body contact applications, a PHEMA is used which is made from an optical grade HEMA monomer. This optical grade HEMA monomer may, for example, have a purity of 99% and be expensive to produce and acquire. In the embodiments described within, PHEMA made from a HEMA monomer having a purity of between about 96% to about 98% can be used with good results.

Figure 1:
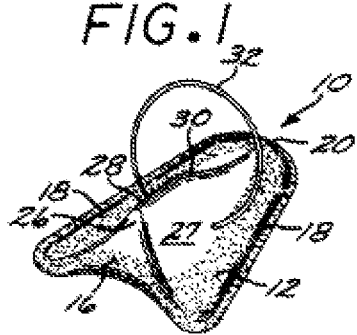
FIG. 1 is a perspective view of a female urinary incontinence device, in accordance with a first embodiment.
Figure 3:
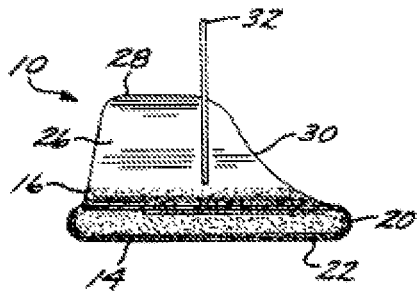
FIG. 3 is a side elevational view of the device of FIG. 1.

The side of the body 12 opposite the base 14 includes a central longitudinal stiffening ridge 26 which forms the thickest part of the body 12. If one adopts the convention that the base 14 is the "bottom" of the body 12, then the body 12 can be defined as having a surface 27 opposite the base that slopes "downwardly" from either side of the ridge 26 toward the edges 18, so that there is a gradual reduction in body 12 thickness from the ridge 26 to the edges 18. Viewed another way, the body 12 can be defined as having a cross-sectional shape that narrows from the base 14 to the "top" or apex 28 of the ridge 26. The resulting configuration is such that a lateral cross section of the body 12, taken through the ridge 26, produces a shape resembling a triangle with rounded corners and slightly concave sides, as shown in FIG. 6. Similarly, the ridge 26 has an anterior edge 30 that tapers "downwardly" from the apex 28 toward anterior end 20 of the body 12, as shown in FIG. 3, so that the anterior end 20 of the body 12 is substantially reduced in thickness as compared to the posterior end 16.

The female urinary incontinence device 10 may be provided with a handle or tab that is either integrally molded with the body 12, or subsequently attached to it. In the first embodiment, handle is a ring or loop 32, for example of thread, that is inserted laterally through the body 12. The loop may be located near the anterior portion of the apex 28 of the ridge 26, depending on the embodiment.

FIGS. 5 and 6 show the female urinary incontinence device 10 installed in the external genitalia of a human female. The female urinary incontinence device 10 is installed so that the base 14 is seated against the vestibule 34 of the vulva 36, anteriorly of the vaginal orifice 37, thereby occluding the urethral meatus 38. The adhesive surface 23, provided by the adhesive layer 22 on the base 14, is configured to seal the urethral meatus 38 to prevent the escape of urine. The lateral edges 18 and the anterior end 20 of the body 12 are tucked under the labia minora 40. The engagement between the labia minora 40 and the sloping surface 27 enhances the retention of the body 12 in engagement with the vestibule 34. The concavity in the posterior end 16 of the body 12 allows for somewhat greater surface area for engagement by the labia minora 40, while leaving a clearance for the vaginal opening 37. The ridge 26 extends into the interlabial space, and the loop 32 protrudes from between the labia majora (not shown), so as to be exposed to facilitate manual grasping, for removal of the female urinary continence device 10.

The body 12 can be provided in a number of sizes to fit a large variety of individuals. The length of the body 12 can be made to be approximately the same as the distance between the anterior lip of the vaginal orifice and the juncture of the labia minora 40. The width of the body 12 may be chosen to conform substantially to the width of the vestibule 34. Predetermined sizes can be trimmed individually for optimum fit. In some cases, a mold of the relevant portions of the vulva may be taken prior to sizing the pad.

The adhesive layer 22 not only provides a fluid-tight seal for the urethral meatus 38, but it also minimizes slippage of the female urinary incontinence device 10. The central ridge 26 lends rigidity that resists deformation of the body 12 and rupture of the adhesive layer 22 under fluid pressure from the urethra, thereby enhancing the fluid-tight seal provided by the body 12 against the urethral meatus 38. It may be chosen to extend the adhesive layer 22 onto the labia-engaging surface 27, thereby further enhancing the stability of the female urinary incontinence device 10.

A female urinary incontinence device 10 constructed in accordance with the first embodiment, as described above, can be made to withstand short-term fluid pressures from the urethra in the range of up to at least about 100, and preferably about 170, centimeters of water without significant leakage, as least for a short period of time. For example, for about two seconds or greater, and preferably about three seconds or greater. Pressures on this order are those that would typically result in involuntary urine voiding in cases of stress and urge incontinence. 170 centimeters of water is the approximate maximum bear-down pressure for a typical adult human female.

As an option, the foam material of the body 12, and/or the adhesive surface 23, can be provided with a medically-active composition. An antibacterial or germicidal agent, such as silver oxide or silver azide may be used, for example.

Figure 8:
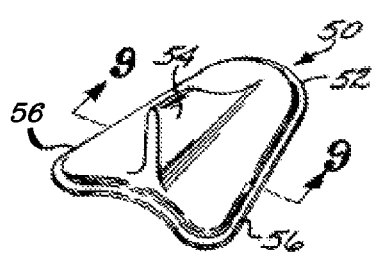
FIG. 8 is a perspective view of a second modified form of the first embodiment.
Figure 9:
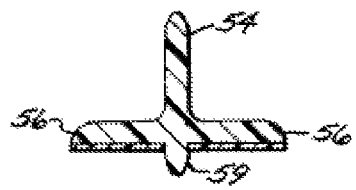
FIG. 9 is cross-sectional view taken along Line 9-9 of FIG. 8.
Figure 10:
FIG. 10 is a cross-sectional view, similar to that of FIG. 9, showing the flexing of the lateral edges of the body of the female urinary incontinence device in accordance with the first embodiment.
Figure 11:
FIG. 11 is a cross-sectional view of a third modified form of the first embodiment.
Figure 12:
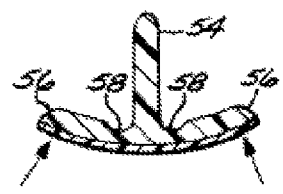
FIG. 12 is a cross-sectional view, similar to that of FIG. 11, showing the flexing of the lateral edges of the body.

The first embodiment lends itself to several modifications that may provide better comfort for certain individuals. For example. FIGS. 8, 9, and 10 show a modified device 50, which includes a body 52 of substantially uniform thickness, except for a longitudinal ridge 54. This modification provides lateral flaps 56 that flex more easily than those of the embodiment of FIGS. 1-7 when engaged against the labia minora 40, thereby yielding a better conformal fit with the genitalia. Still greater flexibility may be provided by forming a longitudinal groove 58 in each of the flaps 56, on either side of the ridge 54, as shown in FIGS. 11 and 12.

As still another option, a short protuberance 59 may be provided on the base 14, as shown in FIGS. 9 and 10. The protuberance 59 is dimensioned to be received wholly or partially within the urethral meatus 38, thereby facilitating proper placement of the female urinary incontinence device 10, and enhancing the occlusion of the urethral meatus 38.

Another modification of the first embodiment is shown in FIGS. 17, 18, and 19. As shown in these figures, a modified female urinary incontinence device 60 includes a layer 62 of highly-absorbant hydrophilic material adjacent the adhesive layer 64 on the base of the female urinary incontinence device 60. The hydrophilic layer 62 can be a mixture of the PHEMA/PEG adhesive and either a microsponge material, such as carboxymethylcellulose (CMC) or a super-absorbant material, such as potassium polyacrylate. The hydrophilic layer 62 draws moisture from the adhesive layer 64 and absorbs the moisture, thereby prolonging the useful lifetime of the adhesive by delaying saturation. Absorption of moisture causes the hydrophilic layer 62 to swell, as shown in FIG. 19, which may enhance the sealing properties of the female urinary incontinence device 60.

Still another modification of the first embodiment is shown in FIGS. 20, 21 and 22. In these figures, a modified female urinary incontinence device 70 has a body 72 having an integral longitudinal ridge 74. The ridge 74 a finger hole 76 in its posterior edge. The finger hole 76 may normally be in a collapsed state, as shown in FIG. 20. It may expand to receive the user's finger 78, as shown in FIG. 22, to facilitate installation and removal.

In FIG. 21, the female urinary incontinence device 70 is shown as having an adhesive layer 80 applied directly to the base of the body 72, as previously described. FIG. 23 shows still another feature that can be incorporated, as a further modification, into any of the previously-described variations of the first embodiment. In this variation or modification, a scrim layer 90 is enclosed within the adhesive 92 applied to the base of the body 72. The scrim layer 90 may be a thin, non-woven sheet of polyester that can reinforce an elastomeric material. In the present embodiment, the scrim layer 90 adds structural integrity to the adhesive material, thereby enhancing the durability of the female urinary incontinence device 70. As shown in FIG. 23, the scrim layer 90 is placed in the adhesive before the adhesive is cured to a semi-solid. Alternatively, the scrim layer 90 can be applied to the base of the body 72 before the adhesive is applied, in which case the scrim layer would be sandwiched between the adhesive and the base of the pad.

Figure 13:
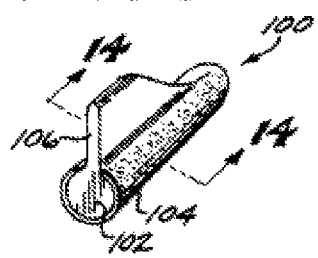
FIG. 13 is a perspective view of a second embodiment.
Figure 14:
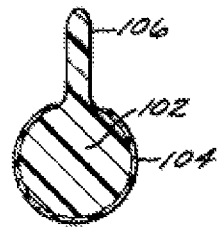
FIG. 14 is a cross-sectional view taken along Line 14-14 of FIG. 13.
Figure 15:
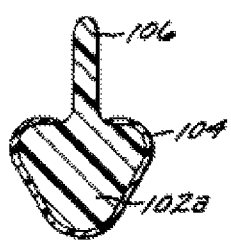
FIG. 15 is a cross-sectional view, similar to that of FIG. 14, showing a modified form of the second embodiment.
Figure 16:
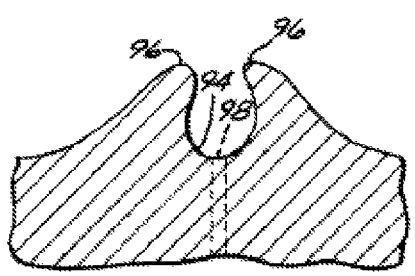
FIG. 16 is a cross-sectional view of the external female genitalia, showing a vestibule of the configuration for which the second embodiment is adapted.

It has been noted that some potential users of the embodiments disclosed have a relatively narrow vestibule floor. This type of anatomical structure is shown in FIG. 16, which shows a simplified cross-sectional view of external female genitalia, wherein the vestibule floor 94 and the labia minora 96 define a relatively narrow space proximate the urethral meatus 98. For those with this type of anatomical structure, the above-described first embodiment may be uncomfortable, or altogether unsuitable. Consequently, a second embodiment, illustrated in FIGS. 13, 14, and 15, is contemplated for such users.

In accordance with this second embodiment, a female urinary incontinence device 100 includes substantially tubular body 102, substantially the entire exterior surface of which is coated with an adhesive 104, of a type described above. The body 102 has a longitudinal ridge 106, for example, not coated with the adhesive, that is used as a gripping element to facilitate installation and removal. As shown in FIGS. 13 and 14, the body 102 may have a substantially elliptical cross-section. Alternatively, as shown in FIG. 15, a body 102a, having a cross-sectional shape similar to a rounded triangle, may be more suitable for some users. Optionally, a protuberance (not shown), such as the protuberance 59 shown in FIGS. 9 and 10 and described above, can be provided on this embodiment to facilitate proper placement and to enhance occlusion.

FIGS. 24 and 25 illustrate a third embodiment. A female urinary incontinence device 110, in accordance with this embodiment, includes a thin, flexible sac or bladder 112, formed of polyurethane or a similar thin, resilient, flexible material. The sac 112 is filled with a suitable biocompatible liquid or gel 114 by means of a needle, and the needle hole is then sealed, thereby forming a compliant sac. A possible material for filling the sac is a hydrogel, similar in some embodiments to the hydrogel adhesives described herein. Substantially the entire exterior surface of the sac is coated with an adhesive 116, of a type described above.

In use, the device 110 is inserted under the labia minora 40 so as to be seated against the floor of the vestibule 34, occluding the urethral meatus 38. The sac conforms to the anatomical structure of the external female genitalia, filling the interlabial space, and sealing against the urethral meatus 38 with the aid of the adhesive 116. Because the sac 112 is so compliant, it can be used for a wide variety of anatomical structures, providing high levels of comfort. The device may be provided with a raised tab 118, not coated with the adhesive 116, to be gripped by the user, to facilitate the installation and removal of the female urinary incontinence device 110.

FIG. 26 illustrates an embodiment of a female urinary incontinence device 120 comprising a body 130 having an anterior end 122, a posterior end 132, and having a central longitudinal ridge 128 carried by the body 130. The body 130 further includes a surface 124 upon which an adhesive layer 134 is carried. In some embodiments, the adhesive layer 134 may comprise a hydrogel as described. In some embodiments, the adhesive layer 134 may substantially cover the surface 124, or may cover, only a portion of the surface. For example, the adhesive layer 134 may cover only a perimeter 136 of the surface, for example the area on the outer extreme of the dashed line a. In some embodiments, the adhesive layer 134 may comprise an adhesive that maintains sufficient sealing engagement to occlude the urethral meatus 38 when exposed to urine having a pH range between about 6.5 and about 8.0. Desired sealing engagement may include the combination of tackiness and total surface area or geometry to seal when exposed to a pressure of up to about 100 centimeters of water. Desired sealing engagement may additionally include the combination of tackiness and total surface area or geometry of the adhesive layer 134 to seal when exposed to a pressure of up to about 170 centimeters of water. Desired sealing engagement may also be referred to as sufficient adhesion strength. In some embodiments, it may be desired that adhesive layer 134 maintains the desired sealing engagement when exposed to urine having a pH of between about 7.5 and about 8.0. This may, for example, correspond to the typical pH range of the urine of a diurnal wearer of the female urinary incontinence device 120 during the evening. In some embodiments, it may be desired that the adhesive layer 134 maintains the desired sealing engagement when exposed to urine having a pH of between about 6.5 and about 7.0. This may, for example, correspond to the typical pH range of the urine of a diurnal wearer of the female urinary continence device 120 during the morning. In some embodiments, it may be desired that the adhesive layer 134 maintain the desired sealing engagement when exposed to urine having a pH of between about 7.5 and about 8.0, but not maintain the desired sealing arrangement when exposed to urine having a pH of between about 6.5 and 7.0. A second feature of the embodiment of FIG. 26 is the presence of a coating 126 which covers a portion of the adhesive layer 134. In some embodiments, the coating 126 may be configured to adhere or otherwise reliably cover the adhesive layer 134, but not have an exposed surface that is tacky or displays adhesive properties on its own. In some embodiments, the coating 126 may be configured to degrade (i.e. disappear or be removed) upon exposure to urine having a pH in a particular range, for example urine having a pH in the range of between about 6.5 and about 7.0. In use, the female urinary incontinence device 120 is placed between the labia minora 40 and the vestibule floor such that the portion of the adhesive layer 134 that is not covered by the coating 126 adheres to the vestibule floor thus causing the female urinary incontinence device 120 to occlude the urethral meatus 38. In some embodiments, the coating 126 may comprise a first coating portion 126a and a second coating portion 126b, with a central adhesive portion 127 configured to adhere directly over the urethral meatus 38. As urine having a pH in the range of between about 6.5 and about 7.0 contacts the coating 126, the coating degrades and thus exposes additional surface area of the adhesive layer 134 that had not previously been exposed, and thus maintains its optimal adhesion strength. This in turn increases the overall adhesion strength of the body 130 by means of the larger adhesive layer 134 area, increasing the usable time of the female urinary incontinence device 120.

Turning to FIG. 28, an embodiment of a female urinary incontinence device 220 comprises a body 230 having an anterior end 222, a posterior end 232, and having a central longitudinal ridge 228 carried by the body 230. The body 230 further includes a surface 224 upon which an adhesive layer 234 is carried. In some embodiments, the adhesive layer 234 may be configured to increase its level of sealing engagement as it is exposed to an increased pH range, for example to about 7.5 to about 8.0. The adhesive layer 234 may also be configured to decrease its level of sealing engagement as it is exposed to an decreased pH range, for example to about 6.5 to about 7.0. One reason for desiring either of these adhesive characteristics separately or both of these two adhesive characteristics together would be to assure that during the day, while the wearer consumes food and beverages, and the pH of the urine is generally higher, the female urinary incontinence device 220 effectively occludes the urethral meatus 38, while in the morning, after fasting which occurs during sleep, at which the pH of the urine is generally lower, the female urinary incontinence device 220 does not effectively occlude the urethral meatus 38, thus signaling to the wearer that a new female urinary incontinence device 220 should be placed. This further assures that the wearer does not leave a single female urinary incontinence device 220 in place for too long of a period, risking infection or other effects of decreased hygiene, and instead places a new female urinary incontinence device 220. In some embodiments, the adhesive layer 234 may comprise polyethylene glycol (PEG), for example a pH activated grade of polyethylene glycol based surgical adhesive. In some embodiments, the adhesive layer 234 may additionally comprise an adhesive that is configured to change color when exposed to urine having a pH in the range between about 6.5 and about 7.0. In some embodiments, the body 230 may be configured to change color when exposed to urine having a pH in the range between about 6.5 and about 7.0. The color change of either the body 230 or the adhesive layer 234 can serve as an indicator to the wearer that it is time to change to a new female urinary incontinence device 220.

Any of the embodiments presented herein may feature partially or completely biodegradable portions, for creating an environmentally-friendly device. FIG. 27 illustrates a biodegradable embodiment of a female urinary incontinence device 140 comprising a body 142, made from biocompatible and biodegradable material, and having an anterior end 144, a posterior end 146, and a central longitudinal ridge 148 carried by the body 142. The body 142 includes one or more upper surfaces 150 and at least one lower surface 152. In some embodiments, the lower surface may be configured to have an adhesive layer 154. A coating 156 is disposed on one or more upper surface 150, and serves to retard the process of biodegradation, by its covering of the one or more upper surface 150. In some embodiments, the coating 156 may also cover some or all of the lower surface 152. For example the lower surface 152 may be covered with the coating 156, and the coating 156 in turn covered by the adhesive layer 154. In some embodiments, the coating 156 may cover a substantial portion of the body 142. For example, it may cover a large amount of the one or more upper surfaces 150 or a large number of the one or more upper surfaces 150, without covering the lower surface 152. In some embodiments, the coating 156 may be configured to degrade with time, or degrade due to one or more particular environmental conditions (pH, % humidity, presence of oxygen). For example, the coating 156 may be configured to begin degrading or to accelerate its degradation process when it is thrown into or flushed down a liquid-based toilet, thus commencing or accelerating the biodegradation of any portion of the body 142. In some embodiments, the coating 156 may comprise a removable layer that is adhered to the body 142. In some embodiments, the removable layer may be peelable from the body 142 by the wearer after the wearer removes the female urinary incontinence device 140, thus allowing the wearer to start or accelerate the biodegradation process, thus minimizing it while the female urinary incontinence device 140 is being used by the wearer. In some embodiments, the female urinary incontinence device 140 may be supplied in a package (not shown) that is hermetically sealed, and configured to be opened by the user prior to using the female urinary incontinence device 140. In some embodiments, the sealed contents of the package may be kept in a vacuum state, in order to delay the effect of the environment, for example oxygen, breaking down the coating 156. In some embodiments, the sealed contents of the package may be filled with a gas with the oxygen being purged. For example, the female urinary incontinence device 140 may be sealed in a package that is filled with a nitrogen gas or argon gas. In some embodiments, the coating 156 may be configured to degrade in a dry, low humidity, environment, and the female urinary incontinence device 140 may be packaged in a package having a semi-aqueous environment or other high humidity environment. While maintained in this environment or while in place on the wearer, the humidity can be high enough to maintain the coating 156, but upon discarding the female urinary incontinence device 140, the dry environment may cause the coating 156 to degrade, thus allowing the biodegradation of the body 142 to occur. In some embodiments, the coating 156 may be water-soluble, and the female urinary incontinence device 140 may be packaged in a package having a dry or low humidity environment. The placement of the female urinary incontinence device 140 on the wearer may begin the process of degrading the coating 156. The typical period of use (for example one day, sixteen hours, eight hours, or four hours) may be short enough such that the biodegradation process is not significantly started until after the female urinary incontinence device 140 is discarded.

Figure 29:
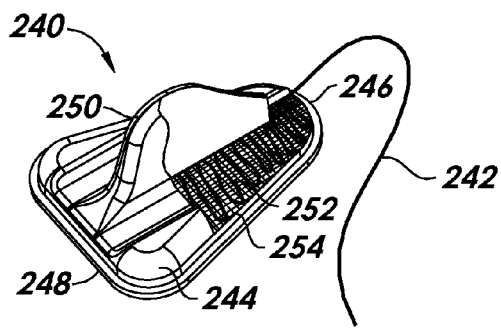
FIG. 29 is a perspective view of an embodiment of a female urinary incontinence device having a tether.

FIGS. 29 through 32 illustrate several embodiments of female urinary incontinence devices having a tether 242. In use, the tether 242 may be used to remove the female urinary incontinence devices. In some embodiments, the tether 242 may be used to manipulate the female urinary incontinence devices. FIG. 29 illustrates a female urinary incontinence device 240 comprising a body 244 having an anterior end 246 and a posterior end 248. A central longitudinal ridge 250 may be carried by the body 244 to aid with the placement of the female urinary incontinence devices 240. In some embodiments, the tether 242 may be molded into the body 244. In some embodiments, the tether 242 may have a back-and-forth, undulating pattern 252, so that it is well incorporated into the body 244, and will not pull out when a tensile force T (FIG. 30) is applied at the end of the tether 242. In some embodiments, a woven fabric 254 may be incorporated into the body 244 to add strength and to lessen the elongation of the body 244 towards the anterior end 246. The woven fabric 254 may reinforce the material of the body 244 and increase its overall tensile strength. In some embodiments, the woven fabric 254 may comprise a scrim. In some embodiments, the tether 242 may be incorporated into the woven fabric 254. In some embodiments, the tether 242 may be partially, substantially or completely woven into the woven fabric 242. In some embodiments, the undulating pattern 252 of the tether 242 may be interwoven into the woven fabric 254. In some embodiments, an adhesive layer 258 (FIG. 30) may be disposed upon a surface 256 of the body 244.

Figure 30:
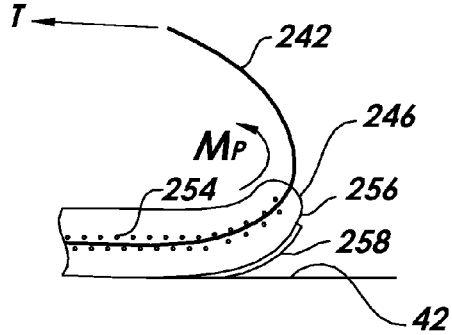
FIG. 30 is a cross-sectional view of an embodiment of the female urinary incontinence device having a tether of FIG. 29 being detached from the vestibule floor.
Figure 31:
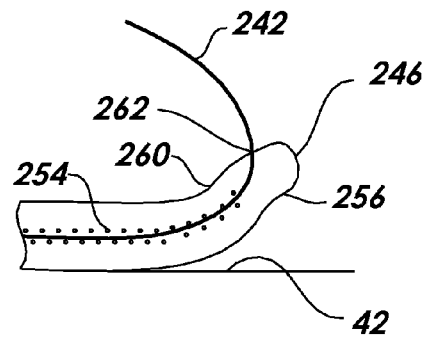
FIG. 31 is a cross-sectional view of an embodiment of a female urinary incontinence device.
Figure 32:
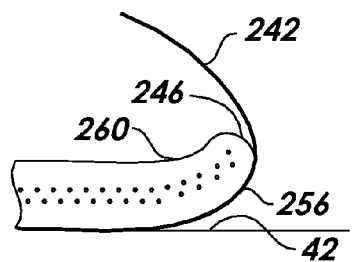
FIG. 32 is a cross-sectional view of an embodiment of a female urinary incontinence device.

In FIG. 30 the tensile force T applied on the tether 242 is applied in a direction generally towards the posterior end 248 of the female urinary incontinence device 240, which, because the tether 242 extends from the anterior end 246 of the female urinary incontinence device 240, cause a peeling moment $M_P$, which causes the adhesive layer 258 to detach (peel) from the vestibule floor 42. In the embodiment of FIG. 30, the tether 242 extends from the anterior end 246 of the body 244. In FIG. 31, the tether 242 extends from an upper portion 260 of the body 244. In some embodiments, as shown in FIG. 31, the tether extends from an upper portion 260 of the body 244, at a point 262 adjacent the anterior end 246 of the body 244. This allows the extending tether 242 to lie completely at the upper portion 260 of the body 244 while the female urinary incontinence device 240 is in place. In FIG. 32, an embodiment is illustrated wherein the tether 242 extends from the anterior end 246 of the body 244, adjacent the lower surface 256 of the body 244. This may lower the tensile stresses in the material of the body 244. In some embodiments, the tether 242 may be incorporated directly into the adhesive layer 258.

Figure 33:
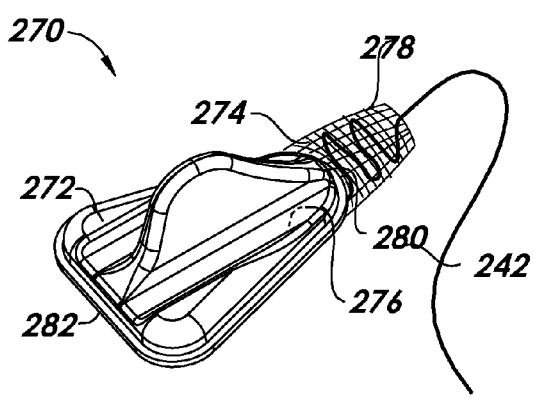
FIG. 33 is a perspective view of an embodiment of a female urinary incontinence device having a tether.

An embodiment of a female urinary incontinence device 270 having an anterior end 280 and a posterior end 282 is illustrated in FIG. 33 in which a woven fabric 274 is partially incorporated into the body 272. A proximal portion 276 of the woven fabric 274 is incorporated into the body 244, or the adhesive layer (not shown), and a distal portion 278 of the woven fabric 274 extends anteriorly from the anterior end 280 of the female urinary incontinence device 270. In some embodiments, the tether 242 may be woven into the woven fabric 274 at only the proximal portion 276 of the woven fabric, at only the distal portion 278 of the woven fabric 274, or at both the proximal portion 276 and the distal portion 278 of the woven fabric 274.

Figure 34:
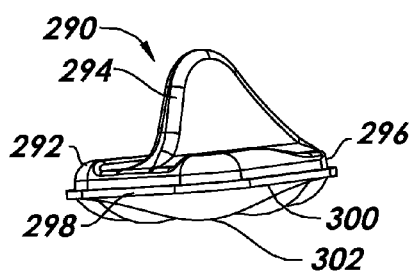
FIG. 34 is a perspective view of an embodiment of preparation device.

FIGS. 34-37 illustrate several embodiments of a system for preparing the area between the labia minora and the vestibule floor prior to the insertion of one of the embodiments of the female urinary incontinence device of the present invention. In FIG. 34, an embodiment of a preparation device 290 comprises a base 292 having a user interface 294. The user interface 294 may include a central longitudinal ridge, a loop, or any other grasping or manipulating structure. The base 292 has an anterior end 296 and a posterior end 298. In some embodiments, the base 292 may have lateral edges. In some embodiments, the base 292 may have a smooth, elliptical or circular shape. In some embodiments, the base 292 may have a wedge shape, or other non-circular shape. The base 292 has a lower surface 300 to which is attached an absorbent structure 302 comprising one or more absorbent materials. In use, the preparation device 290 is removed clean and/or sterile from a package and placed in the region between the labia minora 40 and the vestibule floor 42 cleaning and drying this region. A system for preparing the area between the labia minora 40 and the vestibule floor 42 may include a first preparation device 290 that has a cleaning fluid incorporated into the absorbent structure 302 and a second preparation device 290 that only has a dry absorbent structure 302, so that the first preparation device 290 is used to remove any materials or fluids, and the second preparation device 290 is used to remove moisture. With a clean, dry vestibule floor 42, the adherence of one of the embodiments of the female urinary incontinence device of the present invention is improved. In addition to embodiments of the female urinary incontinence device of the present invention, other devices configured to reside in the region between the labia minora 40 and the vestibule floor 42 may be placed after preparation with one or more preparation devices 290. In some cases, using only a single preparation device 290, for example a preparation device 290 having a dry absorbent structure 302, may be sufficient to prepare the vestibule floor 42 for the female urinary incontinence device. For example, the adhesive layer may have optimum adherence strength with a dry, clean vestibule 42.

Figure 35:
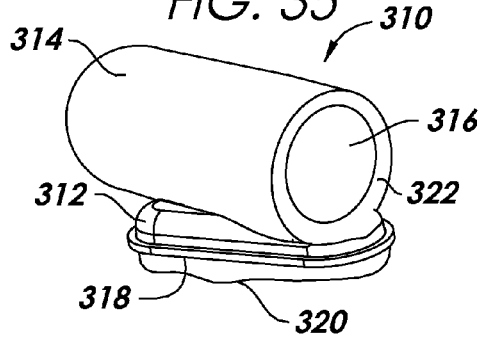
FIG. 35 is a perspective view of an embodiment of a preparation device.

In some embodiments, the absorbent structure 302 is biodegradable. In some embodiments, the base 292 is biodegradable. In some embodiments, the absorbent structure 302 may include a towel or gauze. FIG. 35 illustrates an embodiment of a preparation device 310 comprising a base 312 coupled to a user interface/tubular member 314 having an interior cavity 316 and a wall 322. In some embodiments, the tubular member 314 may comprise a finger cot. In some embodiments, the tubular member 314 may comprise a compliant tube. In some embodiments, the tubular member 314 may be formed from elastic material, such as silicone or polyurethane. The base 312 has a lower surface 318 to which is attached an absorbent structure 320 comprising one or more absorbent materials similar to the absorbent structure 302 described in accordance with FIG. 34.

Figure 36:
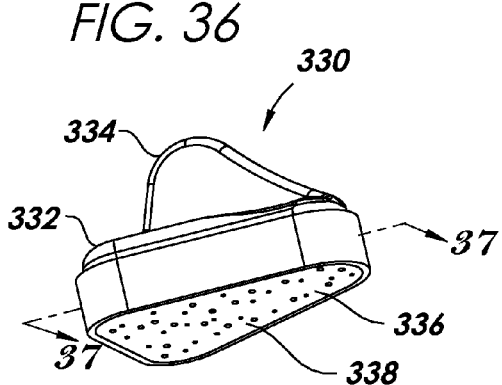
FIG. 36 is a perspective view of an embodiment of a preparation device.
Figure 37:
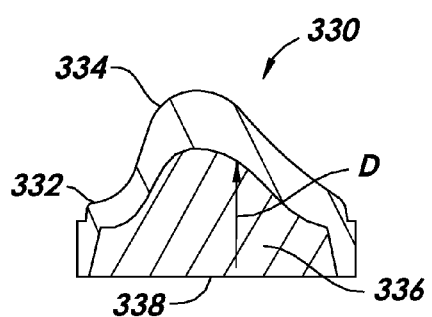
FIG. 37 is a cross-sectional view of the preparation device of FIG. 36 taken along line 37-37 of FIG. 36.

FIG. 36 illustrates an embodiment of a preparation device 330 comprising a base 332 coupled to a user interface 334. The base 332 is hollow, as seen in FIGS. 36 and 37, and is filled with an absorbent structure 336. In some embodiments, the absorbent structure 336 is an open cell foam. In some embodiments, the absorbent structure 336 has capillary action to move moisture away from a lower surface 338 in the direction D.

Figure 38:
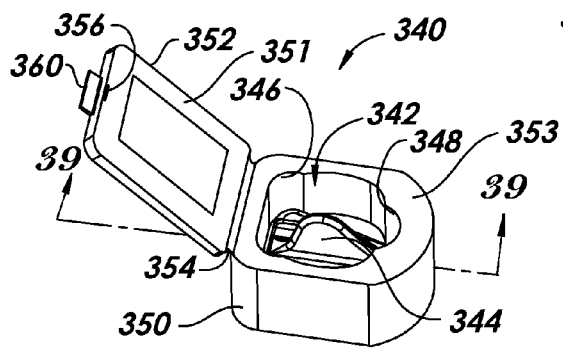
FIG. 38 is a perspective view of an embodiment of a container for a urinary incontinence device.
Figure 39:
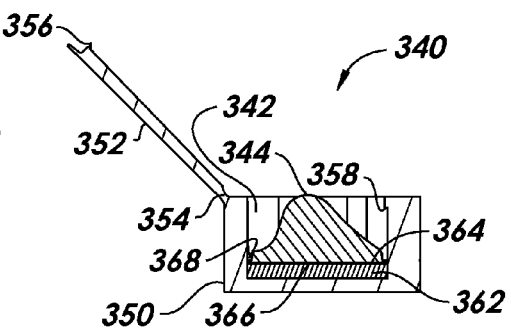
FIG. 39 is a cross-sectional view of the container of FIG. 38 taken along line 39-39 of FIG. 38.

FIGS. 38-41 illustrate several embodiments of a container system for storing, protecting, and desiccating (drying) embodiments of the urinary incontinence devices presented herein, including embodiments of the urinary incontinence devices that are configured to be reusable by the wearer. FIGS. 38-39 illustrate an embodiment of a container 340 comprising a housing 350 having a cavity 342 which is configured for receiving a urinary incontinence device 344. In some embodiments, the cavity may have indentations or contours 346, 348 which are configured to guide or orient the urinary incontinence device 344 while it is placed into the cavity 342 or removed from the cavity 342. In some embodiments, the indentations or contours 346, 348 may have undercuts 368 into which the urinary incontinence device 344 may snap, such that the urinary incontinence device 344 is held in a desired position while the container 340 containing the urinary incontinence device 344 is handled or moved. In some embodiments, the housing 350 may have a cover or protective barrier 352 which may be closed over the housing 350, closing the cavity 342 in a non-sealing, partially sealing or substantially fully sealing manner. In some embodiments, the protective barrier 352 may comprise a hinge 354, for example a traditional hinge, or a living hinge (as shown) which is molded into the housing 350. In some embodiments, the housing 350, protective barrier 352 and hinge 354 may be molded, for example from a polymeric material. In some embodiments, the housing 350, protective barrier 352 and hinge 354 may be created from a 3D process, for example stereolithography, 3D printing, or similar methods. In some embodiments, the housing 350, protective barrier 352 and hinge 354 may be constructed from high strength engineering plastics, or from metal materials. In some embodiments, a snap feature 356 on the protective barrier 352 may interface with a similar snap feature 358 (e.g., an undercut) (FIG. 39) within the cavity 342 to maintain the protective barrier 352 in a closed position. In some embodiments, a tab 360 may be provided on the protective barrier 352 to ease the opening of the protective barrier 352. In some embodiments, a seal 351 may be provided on the protective barrier 352 which follows the contours of the cavity 342 and is configured to interface with a surface 353 of the housing 350 in order to completely or substantially seal the cavity from the ambient atmosphere. In some embodiments, a desiccating material 362 having an interface surface 364 is disposed at the bottom of the cavity 342. In some embodiments, the interface surface 364 of the desiccating material 362 is configured so that the adhesive layer 366 of the urinary incontinence device 344 overlays it and fully contacts it. In this manner, the desiccating material 362 is capable of removing moisture from the adhesive layer 366 (lowering its water content), such that its adhesion strength is increased, and it can be reused. In some embodiments, the desiccating material 362 may be configured to be removable and replaceable with new desiccating material 362, to thus improve the drying capability of the container 340. The desiccating material 362 may comprises a silica gel. In some embodiments, the desiccating material 362 may be configured to be removable and rechargeable (for example by drying within an oven) so that the same desiccating material may be replaced within the cavity 342.

FIG. 40 illustrates an embodiment of a container 370 having a housing 372, cavity 374, and protective barrier 376 which, like container 340 of FIGS. 38-39, is also configured for receiving a urinary incontinence device 344. The container 370 of FIG. 40 includes a gas flow pathway 378 which comprises an inflow portion 380 and an outflow portion 382. The inflow portion 380 may include a desiccation interface or inlet 384, for example for coupling to a dry air source. In some embodiments, the inlet 384 may comprise a barb 386 for attaching to a tubing (not shown) or supply line. The inlet 384 has an internal lumen 388 through which air or other gas may be forcibly driven. The internal lumen 388 communicates with one or more first outlets 390 which open into the cavity 374. One or more second outlets 392 allow the air or other gas to exit from the cavity. The total size and number of the one or more first outlets 390 and one or more second outlets 392 can be adjusted in accordance with an expected specific flow rate and gas viscosity so that the flow of the gas efficiently fills and empties the cavity 374, allowing moisture to be removed. The one or more first outlets 390 and one or more second outlets 392 are shown in FIG. 40 located near the bottom 394 of the cavity 374, such that the highest flow path occurs in proximity to the adhesive layer 366 or the urinary incontinence device 344, maximizing the ability of the gas flow pathway 378 of the container 370 to dry/remove moisture from the adhesive layer 366. In some embodiments, the inlet 384 may be configured to couple to an air pump. In some embodiments, the inlet 384 may be configured to couple to a standard hair dryer. In some embodiments, the inlet 384 may be configured to couple to an industrial heat gun. In an alternative use of the container 370, the inlet 384 may be coupled to a vacuum source, thus becoming an outlet. In this mode, the outflow portion 382 becomes an inflow portion and the inflow portion 380 becomes an outflow portion. This alternative use is optimized if the ambient air is as dry as possible, for example in a room having a heater.

FIG. 41 illustrates an embodiment of a container 400 which is configured to provide its own air flow. The container 400 includes a housing 402 having a cavity 404, and a protective barrier 406 configured to close over the housing 402, enclosing the cavity 404. The housing 402 includes an internal lumen 408 having one more first outlets 410 which allow air enter into the cavity 404. One or more second outlets 412 allow air to exit from the cavity 404. An air circulator 414 is provided, to allow air to flow through the cavity 404, to dry the adhesive layer 366 of the urinary incontinence device 344. The air circulator 414 may be any type of positive pump or even vacuum pump, that allows air to circulate through the cavity 404. In some embodiments, a battery 416 may be provided, or the air circulator 414 may be attached to a wall power outlet.

FIGS. 42 and 43 illustrate an embodiment of a female urinary incontinence device 420 having both urethral occluding and absorbent properties. The female urinary incontinence device 420 comprises a body 430 having an anterior end 422, a posterior end 432, and having a central longitudinal ridge 428 carried by the body 430. As in any of the embodiments of the female urinary incontinence devices presented herein, the central longitudinal ridge 428 may be replaced by any possible user interface, loop, tether, hole, tube, or other type of handle. The female urinary incontinence device 420 includes an adhesive layer 424 which is located around the perimeter of a surface 426 of the body 430. Filling a central hollowed-out portion 434 of the body 430 is an absorbent material 436 having a surface 438 for interfacing directly with the urethral meatus 38. The adhesive layer 424 is configured to adhere to the vestibule floor 42, and force the surface 438 against the urethral meatus 38, but to allow any urine ejected from the urethral meatus 38 to be absorbed by the absorbent material 436. In some embodiments, the absorbent material 436 is an open cell foam. In some embodiments, the absorbent material 436 has capillary action to move moisture away from the surface 438.

FIGS. 44 and 45 illustrate an embodiment of a female urinary incontinence device 520 having both urethral occluding and absorbent properties. The female urinary incontinence device 520 comprises a body 530 having an anterior end 522, a posterior end 532, and having a central longitudinal ridge 528 carried by the body 530. The female urinary incontinence device 520 includes an adhesive layer 524 which is located at a central surface 526 of the body 530. Filling a hollowed-out perimeter portion 534 of the body 530 is an absorbent material 536 having a surface 538 for interfacing directly with the urethral meatus 38. The adhesive layer 524 is configured to adhere to the vestibule floor 42 against the urethral meatus 38. Any urine that overcomes the seal between the adhesive layer 524 and the urethral meatus 38 can be absorbed by the absorbent material 536. In some embodiments, the absorbent material 536 is an open cell foam. In some embodiments, the absorbent material 536 has capillary action to move moisture away from the surface 538.

Figure 46:
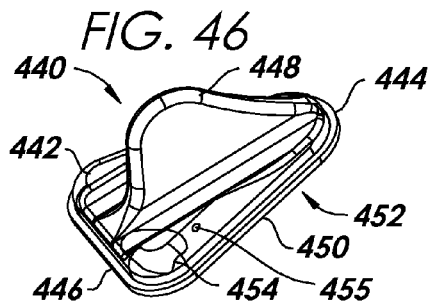
FIG. 46 is a perspective view of an embodiment of a female urinary incontinence device.

FIG. 46 illustrates an embodiment of a female urinary incontinence device 440 comprising a body 442 having an anterior end 444, a posterior end 446, and having a central longitudinal ridge 448 carried by the body 442. The body 442 further includes a surface 450 upon which an adhesive layer 452 is carried. In some embodiments, the adhesive layer 452 may comprise a hydrogel as described herein. A substance 454 is carried by the female urinary incontinence device 440, for example, either directly on the body 442 or on the adhesive layer 452, wherein the substance 454 is configured for controlling the odor of the area associated with both the urethral area and the vaginal area of the wearer. The substance 454 may be configured to lessen, block, mask or completely eliminate one or more types of odors in the area associated with either the urethral area or the vaginal area of the wearer. In some embodiments, the substance 454 may be configured to control vaginal-created odors, for example, odors associated with vaginal discharge. In some embodiments the substance 454 may be configured to control urethra-created odors, for example urethral tract odor. In some embodiments, the substance 454 may be configured to control sweat gland-created odors. In some embodiments the substance 454 may be configured to control a combination of these odors. In some embodiments the substance 454 comprises a coating. In some embodiments the substance 454 is configured to degrade over time. In some embodiments, the substance 454 may include one or more heat-reactive deodorant particles. In some embodiments, the substance 454 may include aluminum chloride or aluminum chlorohydrate. In some embodiments, the substance 454 may include one or more of the following substances having deodorant or anti-perspirant properties: aluminum sesquichlochlorohydrate, aluminum chlorohydrex PG, aluminum zirconium trichlorohydrate, aluminum zirconium trichlorohyrdrex Gly, aluminum zirconium tetrachlorohydrate, aluminum zirconium tetrachlorohydrex Gly, aluminum zirconium tetrachlorohydrex Gly solution, aluminum zirconium pentachlorohydrate. In some embodiments, the body 442 may comprise a foam, and the substance 454 may be embedded or impregnated within the foam. In some embodiments, at least one of the body 442 and the adhesive layer 452 is configured to elute the substance 454. In some embodiments, the substance 454 may be contained within a pellet 455. For example, a pellet 455 may be a time release pellet or a pellet configured to release the substance 454 when one or more specific atmospheric condition is reached (temperature, humidity, pressure).

In some embodiments, the substance 454 may include one or more fragrances. In some embodiments, the substance 454 may include an aldehydic fragrance. In some embodiments, the substance 454 may include an oil, for example one or more of the following oils: lavender oil, rose hip oil, or lemon verbena oil. In some embodiments, the substance 454 may include vitamin E. In some embodiments, the substance 454 may include an odor neutralizer, for example an odor neutralizer comprising activated charcoal. In some embodiments, the substance 454 may even comprise a flavor, for example a pleasing flavor or a neutral flavor which does not interfere with or which even enhances sexual relations. A coating 126, 156 may be used in some cases to temporarily cover the substance 454, or a portion of the body 442 that contains the substance 454. The coating 126, 156 may be configured to degrade or slough off with time, or by exposure to particular pH or humidity, thus delaying the release, exposure or effect of the substance 454.

Figure 47:
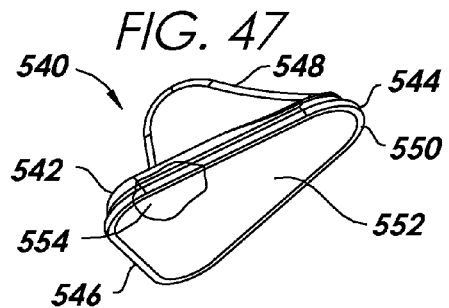
FIG. 47 is a perspective view of an embodiment of a female urinary incontinence device.

FIG. 47 illustrates an embodiment of a female urinary incontinence device 540 comprising a body 542 having an anterior end 544, a posterior end 546, and having a central longitudinal ridge 548 carried by the body 542. The body 542 further includes a surface 550 upon which an adhesive layer 552 is carried. In some embodiments, the adhesive layer 552 may comprise a hydrogel as described herein. A substance 554 is carried by the female urinary incontinence device 540, for example, either directly on the body 542 or on the adhesive layer 552, wherein the substance 554 is configured for medical treatment. In some embodiments, the substance 554 is configured for treatment of vaginal disorders. In some embodiments, the substance 554 is configured for treatment of urethral disorders. In some embodiments, the substance 554 is configured for treatment of reproductive disorders. In some embodiments, the substance 554 is configured as a birth control treatment. In some embodiments, the substance 554 is configured for treatment of dermatological disorders. In some embodiments, the substance 554 includes estrogen. In some embodiments, the substance 554 includes estrogen cream. In some embodiments, the substance 554 includes phytoestrogen. In some embodiments, the substance 554 includes testosterone. In some embodiments, the substance 554 includes salicylic acid. In some embodiments, the substance 554 includes vitamin A. In some embodiments, the substance 554 includes metronidazole. In some embodiments, the substance 554 includes an antibiotic. In some embodiments, the substance 554 includes one or more of the following antibiotics: amoxicillin, ciprofloxacin, ampicillin, levofloxacin, sulfamethoxazole-trimethoprim, or nitrofurantoin. In some embodiments, the substance 554 includes collagen. In some embodiments, the body 542 may comprise a foam, and the substance 554 may be embedded or impregnated within the foam. In some embodiments, at least one of the body 542 and the adhesive layer 552 is configured to elute the substance 554. In some embodiments, the substance 554 may be contained within a pellet. For example, a pellet may be a time release pellet or a pellet configured to release the substance 554 when one or more specific atmospheric condition is reached (temperature, humidity, pressure). In some embodiments, the dosage, concentration or amount of the substance 554 may be chosen based on the expected time of day of wearing the female urinary incontinence device 540. In some embodiments, the substance 554 may configured such that the wearer of to the female urinary incontinence device 540 can apply the substance 554 to the female urinary incontinence device 540 herself. In some embodiments, the female urinary incontinence device 540 may include a specific quantity of the substance 554, which can be modified by the wearer. For example, a portion of the substance 554 may be removable by the wearer, to reduce the amount of substance 554 present on the female urinary incontinence device 540. A coating 126, 156 may be used in some cases to temporarily cover the substance 554, or a portion of the body 542 that contains the substance 554. The coating 126, 156 may be configured to degrade or slough off with time, or by exposure to particular pH or humidity, thus delaying the release, exposure or effect of the substance 554.

Figure 48A:
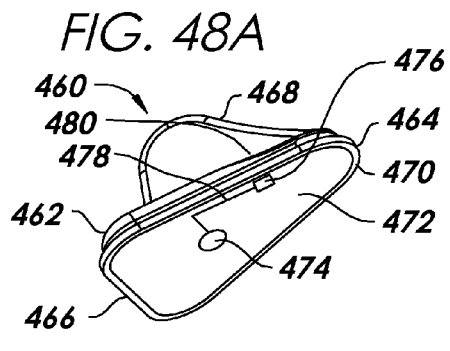
FIG. 48A is a perspective view of an embodiment of a female urinary incontinence device.

FIGS. 48A-48E illustrate several embodiments of female urinary incontinence devices having sensors. FIG. 48A illustrates an embodiment of a female urinary incontinence device 460 comprising a body 462 having an anterior end 464, a posterior end 466, and having a central longitudinal ridge 468 carried by the body 462. The body 462 further includes a surface 470 upon which an adhesive layer 472 is carried. A pH sensor 474 is carried upon the surface 470 of the body 462 and is configured for measuring the pH of the general area. The pH sensor 474 may be located in the desired location with which it is to interface, for example in proximity to the urethral meatus 38. An interface 476 is connected to the pH sensor 474 by a connector 478, which may include a conductive trace or a conductive wire. In some embodiments, the interface 476 may include an RFID chip for storing information. The RFID chip may be powered from an external source. In some embodiments, the interface 476 may include a port which is accessible from an upper portion 480 of the body 462. In embodiments wherein the pH sensor 474 is adjacent the surface 470 of the body 462, the pH of the urine may be measured. Alternatively, in embodiments wherein the pH sensor 474 is adjacent the upper portion 480 of the body 462 or in other areas more remote from the urethral meatus 38, the pH of the local environment may be measured. This, for example, may be helpful in assessing yeast infections. In some embodiments, the pH sensor 474 may be used to determine when it is time to replace or dessicate the female urinary incontinence device 460. In some embodiments, the pH sensor 474 may be used determine whether a particular medical take by the wearer is having the desired effect, or too severe an effect. In some embodiments, the pH sensor 474 may be used to indicate the likelihood or forming one or more kidney stones.

Figure 48B:
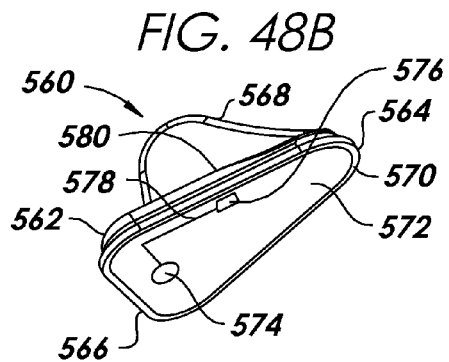
FIG. 48B is a perspective view of an embodiment of a female urinary incontinence device.

FIG. 48B illustrates an embodiment of a female urinary incontinence device 560 comprising a body 562 having an anterior end 564, a posterior end 566, and having a central longitudinal ridge 568 carried by the body 562. The body 562 further includes a surface 570 upon which an adhesive layer 572 is carried. A temperature sensor 574 is carried upon the surface 570 of the body 562 and is configured for measuring the temperature of the general area. The temperature sensor 574 may be located in the desired location with which it is to interface, for example in proximity to the urethral meatus 38. An interface 576 is connected to the temperature sensor 574 by a connector 578, which may include a conductive trace or a conductive wire. In some embodiments, the interface 576 may include an RFID chip for storing information. The RFID chip may be powered from an external source. In some embodiments, the interface 576 may include a port which is accessible from an upper portion 580 of the body 562. In some embodiments, the temperature sensor 574 may be used to sense the presence of fever. In some embodiments, the temperature sensor 574 may be used by persons intending to practice certain aspects of the "rhythm method" of birth control. In some embodiments, the temperature sensor 574 may be located adjacent the posterior end 566 of the female urinary incontinence device 560, in order to be closer to the vaginal orifice 37 (FIG. 5). The temperature sensor 574 may comprise a number of different temperature sensor technologies. In some embodiments, the temperature sensor 574 may comprise a thermistor. In some embodiments, the temperature sensor 574 may comprise a thermocouple.

Figures 48C, 48D, 48E:
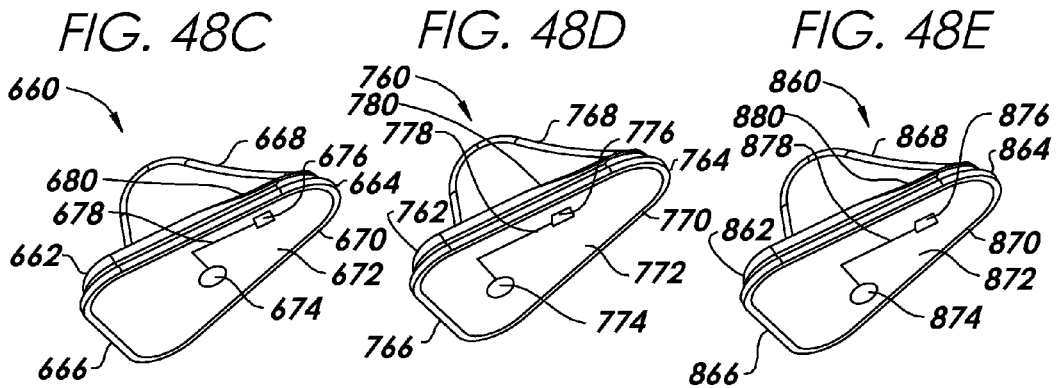
FIG. 48C is a perspective view of an embodiment of a female urinary incontinence device.
FIG. 48D is a perspective view of an embodiment of a female urinary incontinence device.
FIG. 48E is a perspective view of an embodiment of a female urinary incontinence device.

FIG. 48C illustrates an embodiment of a female urinary incontinence device 660 comprising a body 662 having an anterior end 664, a posterior end 666, and having a central longitudinal ridge 668 carried by the body 662. The body 662 further includes a surface 670 upon which an adhesive layer 672 is carried. A moisture sensor 674 is carried upon the surface 670 of the body 662 and is configured for measuring the humidity or water content of the general area. The moisture sensor 674 may be located in the desired location with which it is to interface, for example in proximity to the urethral meatus 38. An interface 676 is connected to the moisture sensor 674 by a connector 678, which may include a conductive trace or a conductive wire. In some embodiments, the interface 676 may include an RFID chip for storing information. The RFID chip may be powered from an external source. In some embodiments, the interface 676 may include a port which is accessible from an upper portion 680 of the body 662. In some embodiments, the moisture sensor 674 may be used to sense the presence of a leak between the surface 670 and the urethral meatus 38. In some embodiments, the moisture sensor 674 may comprise a hydrometer. In some embodiments, the moisture sensor 674 may be configured to calculate a dielectric constant.

FIG. 48D illustrates an embodiment of a female urinary incontinence device 760 comprising a body 762 having an anterior end 764, a posterior end 766, and having a central longitudinal ridge 768 carried by the body 762. The body 762 further includes a surface 770 upon which an adhesive layer 772 is carried. A pressure sensor 774 is carried upon the surface 770 of the body 762 and is configured for measuring the pressure of the general area. In some embodiments, the pressure sensor 774 is configured to measure the pressure within the area sealed by the adhesive layer 772. The pressure sensor 774 may be located in the desired location with which it is to interface, for example adjacent the urethral meatus 38. An interface 776 is connected to the pressure sensor 774 by a connector 778, which may include a conductive trace or a conductive wire. In some embodiments, the interface 776 may include an RFID chip for storing information. The RFID chip may be powered from an external source. In some embodiments, the interface 776 may include a port which is accessible from an upper portion 780 of the body 762. In some embodiments, the pressure sensor 774 may be used to sense the presence or amount of leak between the surface 770 and the urethral meatus 38. Pressure sensors and methods for forming pressure sensors may be used in certain embodiments such as those described in U.S. publication No. 2014/0350348, filed May 22, 2014, and entitled "Passive and Wireless Pressure Sensor," which is hereby incorporated by reference in its entirety for all purposes.

FIG. 48E illustrates an embodiment of a female urinary incontinence device 860 comprising a body 862 having an anterior end 864, a posterior end 866, and having a central longitudinal ridge 868 carried by the body 862. The body 862 further includes a surface 870 upon which an adhesive layer 872 is carried. A pyrogen sensor 874 is carried upon the surface 870 of the body 862 and is configured for measuring the presence of pyrogens of the general area. The pyrogen sensor 874 may be located in the desired location with which it is to interface, for example adjacent the urethral meatus 38. An interface 876 is connected to the pyrogen sensor 874 by a connector 878, which may include a conductive trace or a conductive wire. In some embodiments, the interface 876 may include an RFID chip for storing information. The RFID chip may be powered from an external source. In some embodiments, the interface 876 may include a port which is accessible from an upper portion 880 of the body 862. In some embodiments, the pyrogen sensor 874 may be simply be a temperature sensor, like the temperature sensor 574 of the embodiment of the female urinary incontinence device 560 of FIG. 48B.

Figure 49:
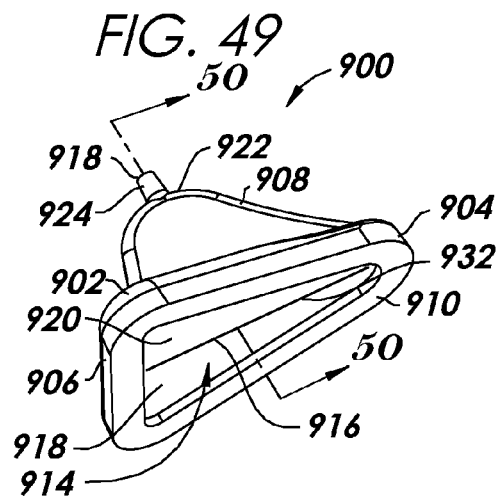
FIG. 49 is a perspective view of an embodiment of a female urinary incontinence device.
Figure 50:
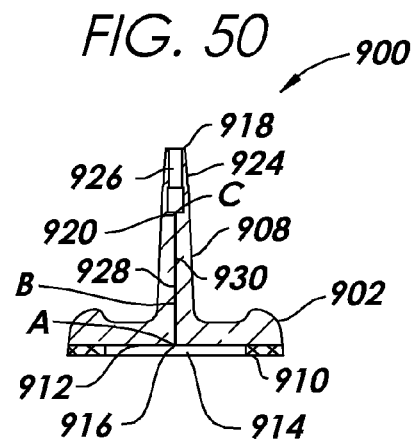
FIG. 50 is a cross-sectional view of the female urinary incontinence device of FIG. 49 taken along line 50-50 of FIG. 49.
Figure 51:
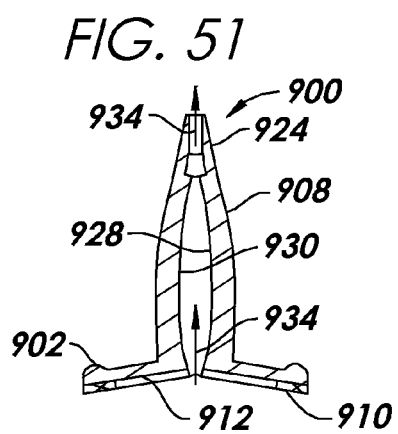
FIG. 51 is a cross-sectional view of the female urinary incontinence device of FIG. 49 during sustained voiding.

FIGS. 49-51 illustrate an embodiment of a female urinary incontinence device 900 comprising a body 902 having an anterior end 904, a posterior end 906, and having a central longitudinal ridge 908 carried by the body 902. As in any of the embodiments of the female urinary incontinence devices presented herein, the central longitudinal ridge 908 may be replaced by any possible user interface, loop, tether, hole, tube, or other type of handle. The female urinary incontinence device 900 includes an adhesive layer 910 which is located around the perimeter of a surface 912 of the body 902. A central portion 914 includes a slit 916 separating a portion of the body 902 into a first body portion 918 and a second body portion 920. Though the slit 916 may extend in any direction, in the embodiment depicted in FIGS. 49-51, it extends longitudinally between the anterior end 904 and the posterior end 906. Because the slit 916 does not extend completely through the anterior end 904 or the posterior end 906, and also does not extend completely through the adhesive layer 910, the slit opens into a closed passageway 920 within the body, between the surface 912 and the dorsal tip 918 of the central longitudinal ridge 908. The slit 916 may simply terminate at the upper surface 922 of the central longitudinal ridge 908, or as depicted in FIGS. 49-51, the slit 916 may transition into a nozzle 924 having a lumen 926. The length of the slit 916 (from anterior to posterior) may be constructed to narrow as it extends towards the upper surface 922 of the central longitudinal ridge 908 to match the outer contours of the central longitudinal ridge and thus to maintain the wall thickness of the body 902 and the central longitudinal ridge 908 on either side of the slit 916. In use, the adhesive layer 910 is configured to adhere to the vestibule floor 42, and force the surface 912 adjacent or against the urethral meatus 38. The body 902 and central longitudinal ridge 908 have two opposing internal walls 928, 930 at the slit 916. A portion (from point A to point B) or all (from point A to point C) of the dorsal extent of the internal walls 928, 930 may be adhered to one another, for example by an adhesive. The adherence of the two internal walls 928, 930 to each other creates a sealed barrier 932 through which urine in short (acute) bursts of pressure, for example from sudden spikes in abdominal pressure from sneezing, coughing or exercise, may not pass. However, the sealed barrier 932, when exposed to an extended pressurization, for example from active purposeful voiding, will open (by the separation of the two internal walls 928, 930, as seen in FIG. 51), thus allowing urine to pass along a flow path 934 from the surface 912 through the slit 916, through the lumen 926 and out the end of the nozzle 924. The nozzle 924 may be aim-able, or may even be attachable to a tube (not shown) to aid controlling the flow of the urine being voided. For example, the inner diameter of the tube may be forced over a barb (not shown) on the nozzle 924. After the purposeful voiding is complete, the two internal walls 928, 930 can re-adhere to each other, thus recreating the sealed barrier 932 that is able to resist sudden spikes in abdominal pressure.

The sealed barrier 932 may alternatively be an uncut portion of the slit 916. For example, an uncut portion over a portion of thickness at the surface 912. The slit 916 may be molded, or may be cut after molding the female urinary incontinence device 900. The uncut portion may be configured (for example, by controlling its material or thickness) to only pull apart with extended stress due to active voiding. The slit 916 itself may alternatively be a molded lumen that does not have a slit shape, for example a circular cross-section, oval cross-section or other cross-section lumen. The lumen may have adhesive inside it, or may be fused at a portion so that it performs as described in relation to acute and extended events.

Figure 52:
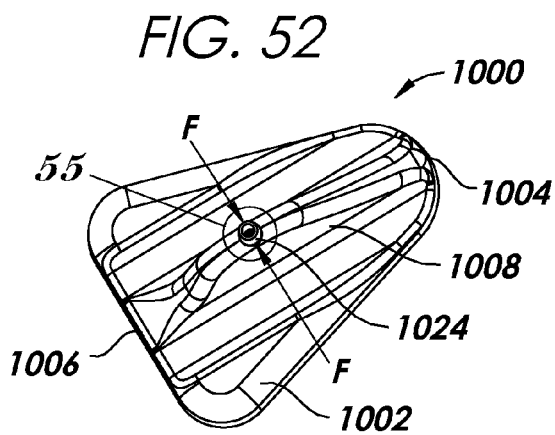
FIG. 52 is a perspective view of an embodiment of a female urinary incontinence device.
Figure 53:
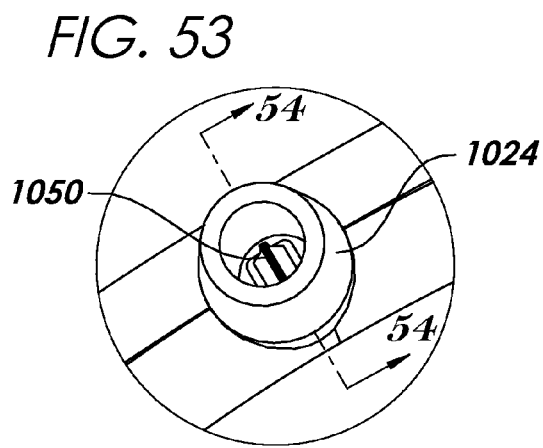
FIG. 53 is a detail view including a valved feature of the female urinary incontinence device of FIG. 52.
Figure 54:
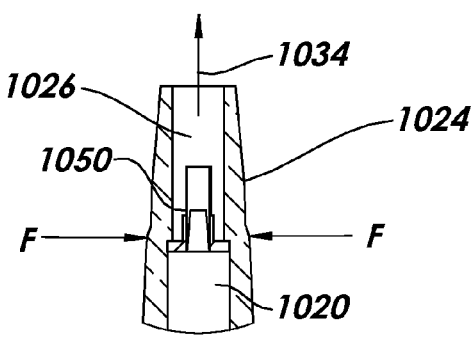
FIG. 54 is a cross-sectional view of the female urinary incontinence device of FIG. 53 taken along line 54-54 of FIG. 53.

FIGS. 52-54 illustrate an embodiment of a female urinary incontinence device 1000 comprising a body 1002 having an anterior end 1004, a posterior end 1006, and having a central longitudinal ridge 1008 carried by the body 1002. As in any of the embodiments of the female urinary incontinence devices presented herein, the central longitudinal ridge 1008 may be replaced by any possible user interface, loop, tether, hole, tube, or other type of handle. The female urinary incontinence device 1000 includes an adhesive layer (not shown) and passageway 1020, and operates much the same way as the embodiment of the female urinary incontinence device 900 described in FIGS. 49-51. The female urinary incontinence device 1000 may or may not include the sealed barrier of the female urinary incontinence device 900 described in FIGS. 49-51. The female urinary incontinence device 1000 has a nozzle 1024 which contains a valve 1050 which is sealed within the lumen 1026. The valve 1050 may comprise a duckbill valve (as depicted) or any other valve that may be made small, and be openable. The valve may be opened from a closed state to an open state by the wearer by applying manual pressure, or force F, to opposing sides of the nozzle 1024 or any other structure of the body 1002 adjacent the valve 1050. The nozzle 1024 structure, may include snaps which allow the valve 1050 to stay in the open state after having been manually opened, and the allow the valve to be closed into a closed state by reapplying the force F, thus undoing the snap. The valve 1050 allows the wearer to periodically void some or all of the contents of the bladder of urine at chosen times (for example into a toilet) without removing the female urinary incontinence device 1000. Flow path 1034 indicates the flow of voided urine. Alternatively, the valve may be configured to open at a selected pressure, for example about 170 cm of water or about 100 cm of water.

FIGS. 55 and 56 illustrate an embodiment of a female urinary incontinence device 1060 comprising a body 1062 having an anterior end 1064, a posterior end 1066, and having a central longitudinal ridge 1068 carried by the body 1062. As in any of the embodiments of the female urinary incontinence devices presented herein, the central longitudinal ridge 1068 may be replaced by any possible user interface, loop, tether, hole, tube, or other type of handle. In some embodiments, substantially the entire female urinary incontinence device 1060 from a first surface 1070 to a dorsal end 1072 is made from a silicone hydrogel. In some embodiments, the silicone hydrogel may comprise a water gradient silicone hydrogel, which, when hydrated, has a first water content at the first surface 1070 and a second water content at the dorsal end 1072. In some embodiments, the water gradient silicone hydrogel may have a first water content at the first surface 1070 and a second water content at the central longitudinal ridge 1068. In some embodiments, the first water content may be significantly less than the second water content. For example, the first water content may be lower than the second water content so that the first surface 1070 is tacky and can engage the vestibule floor 34 and/or occlude the urethral meatus 38, while one or more of the the upper surface 1061 of the body 1062, the central longitudinal ridge 1068, and/or the dorsal end 1072 may be lubricious, to aid in comfort. For example, the lubricious upper surface of the body 1062 or the lubricious central longitudinal ridge 1068 may allow portions of the anatomy like the labia majora to slide past and not be chafed or irritated. In some embodiments, the first surface 1070 may be tacky enough to act as the adhesive.

A silicone hydrogel that is capable, when hydrated, of having a water content of 50%, is said to have a 50% water holding capacity. In some embodiments, a first water holding capacity at the first surface 1070 may be less than a second water holding capacity at the central longitudinal ridge 1068 and/or the dorsal end 1072. In some embodiments, this difference is greater than about 10%. In some embodiments, this difference is greater than about 20%. In some embodiments, this difference is greater than about 30%. In some embodiments, this difference is greater than about 40%. In some embodiments, this difference is greater than about 50%. In some embodiments, the range between the first water holding capacity and the second water holding capacity may be between about 30% and about 80%. In some embodiments, the range between the first water holding capacity and the second water holding capacity may be between about 40% and about 70%. In some embodiments, the range between the first water holding capacity and the second water holding capacity may be between about 50% and about 60%. In some embodiments, an internal substrate 1074 may be located between the first surface 1070 and the central longitudinal ridge 1068 and/or the majority of the body 1062. In some embodiments, the silicone hydrogel is cross-linked with ultra-violet (UV) light. In some embodiments, the silicone hydrogel is at least partially masked during the cross-linking with the UV light. In some embodiments, the UV beam is attenuated during the cross-linking with the UV light.

Silicone hydrogels and methods for forming devices from silicone hydrogels may be used in certain embodiments, such as those described in U.S. publication No. 2012/0026458, filed Jul. 29, 2011, and entitled "Silicone Hydrogel Lenses with Water-Rich Surfaces," which is hereby incorporated by reference in its entirety for all purposes. Silicone hydrogels and methods for forming devices from silicone hydrogels may be used in certain embodiments, such as those described in U.S. publication No. 2015/0094393, filed Sep. 23, 2014, and entitled "Method for Making UV-Absorbing Ophthalmic Lenses," which is hereby incorporated by reference in its entirety for all purposes. In some embodiments, a wetting agent may additionally be used, in order to aid the wetting of the silicone hydrogel. In some embodiments, the wetting agent may be an internal wetting agent (within the female urinary incontinence device 1060). In some embodiments, the wetting agent may comprise hyaluronic acid, methacrylated hyaluronic acid, or poly(oxyethylene)-poly(oxybutylene). In some embodiments, the wetting agent may be photocrosslinkable.

In some embodiments, the manufacturing process of the female urinary incontinence device 1060 may be done using reusable molds. In some embodiments, the reusable molds may comprise silica glass. In some embodiments, the reusable molds may comprise quartz. In some embodiments, the reusable molds may comprise a water-soluble polymer. Materials and methods for forming devices may be used in certain embodiments, such as those described in U.S. Pat. No. 5,508,317, filed Aug. 4, 1994, and entitled, "Photocrosslinked Polymers," which is hereby incorporated by reference in its entirety for all purposes. Materials and methods for forming devices may be used in certain embodiments, such as those described in U.S. Pat. No. 6,800,225, filed Jul. 14, 1994, and entitled, "Process and Device for the Manufacture of Mouldings and Mouldings Manufactured in Accordance with that Process," which is hereby incorporated by reference in its entirety for all purposes. Materials and methods for forming devices may be used in certain embodiments, such as those described in U.S. Pat. No. 8,163,206, filed Jun. 16, 2009, and entitled, "Method for Making Silicone Hydrogel Contact Lenses," which is hereby incorporated by reference in its entirety for all purposes.

FIGS. 57 and 58 illustrate another embodiment of a female urinary incontinence device 1100 comprising a silicone hydrogel, such as a water gradient silicone hydrogel. The female urinary incontinence device 1100 comprises a body 1102 having an anterior end 1104, a posterior end 1106, and a tether 1108. The tether 1108 has a first end 1110 and a second end 1112, the first end 1110 of the tether 1108 incorporated into the body 1102 and the second end 1112 configured for grasping, such that a tensile force can be placed on at least a portion of the body to aid its removal from between the labia minora and the vestibule floor. In some embodiments, substantially the entire female urinary incontinence device 1100 from a first surface 1116 to a dorsal end 1118 is made from a water gradient silicone hydrogel. In some embodiments, the water gradient silicone hydrogel is configured such that the first (bottom) surface 1116 has a tacky or sticky characteristic, while the remaining surface 1120 of the body 1102 is not significantly tacky or sticky.

FIGS. 59 and 60 illustrate another embodiment of a female urinary incontinence device 1130 comprising a silicone hydrogel, such as a water gradient silicone hydrogel. The female urinary incontinence device 1130 comprises a body 1132 having an anterior end 1134, a posterior end 1136, and a tether 1142. The tether 1142 may be similar to the tether 1108 previously described. In some embodiments, substantially the entire female urinary incontinence device 1130 from a first surface 1144 to a dorsal end 1146 is made from a water gradient silicone hydrogel. In some embodiments, the water gradient silicone hydrogel is configured such that the a first three-dimensional surface 1140 has a tacky or sticky characteristic, while a second three dimensional surface 1138 is not significantly tacky or sticky. The first three-dimensional surface 1140 is depicted in FIGS. 59 and 60 with an "x" pattern, while the second three dimensional surface 1138 is not. The first three-dimensional surface 1140 may also be described as an adhesive surface a second three dimensional surface 1138 may also be described as a non-adhesive surface. The location of the adhesive and non-adhesive surfaces may be controlled by one or more processes. For example, cornstarch may be controllably applied (e.g., by masks or templates) to the second three-dimensional surface 1138 in order to reduce its tackiness. Other surface treatments may be applied to one or both of the first three-dimensional surface 1140 and/or second three dimensional surface 1138, including but not limited to corona discharge, plasma discharge, cleaning, degreasing, chemical etching, acid etching, mechanical etching, photoetching, application of surface additives, primer application, solvent application, mechanical abrasion, or blasting with particles, including silica-based particles. Any of these processes may be used to alter or control the water holding capacity of first three-dimensional surface 1140 and/or second three dimensional surface 1138.

The resulting female urinary incontinence devices 1130, 1060, 1100 as described, by their improved physical properties may have increased breathability, allowing for improved comfort to the wearer and better skin hydration and moisture control. In addition the wearer may experience better odor control, as the skin demonstrates improved moisture balance. Comfort for the wearer is also increased because of better temperature control. Additionally, if a medicant is infused, absorption of the medicant can be increased and/or optimized.

From the foregoing, the features of the present invention will be readily appreciated. The incontinence device in accordance with the present invention provides effective management of female urinary incontinence, such as stress incontinence, without the inconvenience and discomfort associated with prior art urine collection devices and absorbent pads. The present invention is easy to use and comfortable to wear. It is easily shaped and sized to fit each individual user's anatomy with optimum effectiveness and comfort. Easily and inexpensively manufactured, the present invention can be made as a disposable item.

While embodiments have been shown and described, various modifications may be made without departing from the scope of the inventive concepts disclosed herein.

What is claimed is:

1. A system for managing female incontinence comprising:
   a body of biocompatible material configured to fit between the labia minora and the vestibule floor, the body having a surface configured to occlude the urethral meatus;
   an adhesive carried on at least a first portion of the surface and configured to provide a sealing engagement between the body and the urethral meatus; and
   a substance carried by at least one of the body and the adhesive and configured for controlling the odor of the general vaginal-urethral area of a female,
   wherein the substance is contained within a pellet.

2. A system for managing female incontinence comprising:
   a body of biocompatible material configured to fit between the labia minora and the vestibule floor, the body having a surface configured to occlude the urethral meatus;
   an adhesive carried on at least a first portion of the surface and configured to provide a sealing engagement between the body and the urethral meatus;
   a substance carried by at least one of the body and the adhesive and configured for controlling the odor of the general vaginal-urethral area of a female;
   a manipulation member coupled to at least one of the body and the adhesive and configured to be engaged by at least one finger, wherein the manipulation member comprises a tether coupled to at least one of the body and the adhesive, and wherein the tether comprises a first end and a second end, the first end of the tether incorporated into the at least one of the body and the adhesive and the second end of the tether configured for grasping, such that a tensile force can be placed on at least a portion of the body to aid its removal from between the labia minora and the vestibule floor; and
   a woven fabric incorporated into at least one of the body and the adhesive, wherein the first end of the tether is at least partially combined into the woven fabric.

3. The system of claim 1, wherein the substance comprises one or more heat-reactive deodorant particles.

4. The system of claim 1, wherein the body comprises a foam, and wherein the substance is embedded or impregnated within the foam.

5. The system of claim 1, wherein the substance is configured for controlling urethral tract odor.

6. The system of claim 1, wherein the substance is configured for controlling vaginal odor.

7. The system of claim 6, wherein the vaginal odor is associated with vaginal discharge.

8. The system of claim 1, wherein the substance is configured for controlling sweat gland odor.

9. The system of claim 1, wherein the substance comprises one or more fragrances.

10. The system of claim 1, wherein the substance comprises an oil.

11. The system of claim 10, wherein the oil comprises lavender oil.

12. The system of claim 10, wherein the oil comprises rose hip oil.

13. The system of claim 10, wherein the oil comprises lemon verbena oil.

14. The system of claim 1, wherein the substance comprises vitamin E.

15. The system of claim 1, wherein the substance comprises an odor neutralizer.

16. The system of claim 15, wherein the odor neutralizer comprises activated charcoal.

17. The system of claim 1, wherein the adhesive comprises PHEMA.

18. The system of claim 17, wherein the PHEMA is formed from a HEMA monomer having a purity of about 96% to about 98%.

19. The system of claim 1, wherein the adhesive comprises a silicone hydrogel.

20. The system of claim 19, wherein the silicone hydrogel is a water gradient silicone hydrogel.

21. The system of claim 2, wherein the adhesive comprises PHEMA.

22. The system of claim 21, wherein the PHEMA is formed from a HEMA monomer having a purity of about 96% to about 98%.

23. The system of claim 2, wherein the adhesive comprises a silicone hydrogel.

24. The system of claim 23, wherein the silicone hydrogel is a water gradient silicone hydrogel.

25. The system of claim 2, wherein the body includes a longitudinal ridge.

26. The system of claim 2, wherein the tether is incorporated into the body.

27. The system of claim 26, wherein the tether has an undulating pattern within the body.

28. The system of claim 2, wherein the woven fabric comprises a scrim.

29. The system of claim 2, wherein the tether is partially woven into the woven fabric.

30. The system of claim 2, wherein the tether is at substantially woven into the woven fabric.

* * * * *